US012644105B2

(12) United States Patent
Picher Serantes et al.

(10) Patent No.: US 12,644,105 B2
(45) Date of Patent: Jun. 2, 2026

(54) PHI29 DNA POLYMERASE MUTANTS WITH IMPROVED PRIMER RECOGNITION

(71) Applicant: 4BASEBIO SL, Madrid (ES)

(72) Inventors: Ángel Joaquin Picher Serantes, Madrid (ES); Luis Blanco Dávila, Madrid (ES)

(73) Assignee: 4basebio SL, Madrid (ES)

( * ) Notice: Subject to any disclaimer, the term of this patent is extended or adjusted under 35 U.S.C. 154(b) by 1182 days.

(21) Appl. No.: 17/611,861

(22) PCT Filed: May 15, 2020

(86) PCT No.: PCT/EP2020/063740
§ 371 (c)(1),
(2) Date: Nov. 16, 2021

(87) PCT Pub. No.: WO2020/234200
PCT Pub. Date: Nov. 26, 2020

(65) Prior Publication Data
US 2022/0235337 A1 Jul. 28, 2022

Related U.S. Application Data

(60) Provisional application No. 62/849,252, filed on May 17, 2019.

(51) Int. Cl.
*C12N 9/12* (2006.01)
*C12P 19/34* (2006.01)

(52) U.S. Cl.
CPC ............ *C12N 9/1252* (2013.01); *C12P 19/34* (2013.01); *C12Y 207/07007* (2013.01)

(58) Field of Classification Search
CPC ......... C12N 9/1252; C12N 9/22; C12P 19/34; C12Y 207/07007; C12Q 1/6844; C12Q 1/6869; C12Q 2521/101; C12Q 2533/101
See application file for complete search history.

(56) References Cited

U.S. PATENT DOCUMENTS

| | | | |
|---|---|---|---|
| 5,656,493 A | 8/1997 | Mullis et al. | |
| 11,104,889 B2 * | 8/2021 | Zhang ............ | C12Y 207/07007 |
| 2010/0112645 A1 * | 5/2010 | Clark ................... | C12Q 1/6869 |
| | | | 435/174 |
| 2017/0159033 A1 | 6/2017 | Kamtekar et al. | |
| 2020/0208126 A1 | 7/2020 | Zhougang et al. | |

FOREIGN PATENT DOCUMENTS

| | | |
|---|---|---|
| EP | 2813576 A2 | 12/2014 |
| EP | 3660148 A1 | 6/2020 |
| WO | 2011047307 A1 | 4/2011 |
| WO | 2015148218 | 10/2015 |
| WO | 2018118997 | 6/2018 |
| WO | 2018118997 A2 | 6/2018 |
| WO | 2019019222 A1 | 1/2019 |
| WO | 2020073266 A1 | 4/2020 |

OTHER PUBLICATIONS

Livingstone CD, Barton GJ. Protein sequence alignments: a strategy for the hierarchical analysis of residue conservation. Bioinformatics. Dec. 1, 1993;9(6):745-56. (Year: 1993).*
Intellectual Office of Singapore, Written Opinion for SG Application No. 11202112620T, dated Oct. 2, 2023; 8 pages.
First Examination Opinion Notice for CN 202080036838.X dated May 31, 2024, 9 pages.
Notice of Reasons for Rejection for JP 2021-568525 dated Jun. 10, 2024, 9 pages.
Office Action (English Translation) for CN 202080036838.X dated Jan. 23, 2025, 6 pages.
Blanco, Luis et al. "Characterization and purification of a phage ¢29-encoded DMA polymerase required for the initiation of replication", Proc. National. Academy Sci USA, Biochemistry, vol. 81 pp. 5325-5329, Sep. 1984.
Blanco, Luis et al. "Characterization of a 3'—5' exonuclease activity in the phage ¢29-encoded DNA polymerase"; Nucleic Acids Research, IRL Press Limited, Oxford, England, vol. 13 No. 4, pp. 1239-1249, 1985.
Blanco, Luis et al. "Highly Efficient DNA Synthesis by the Phage ¢29 DNA Polymerase; Symmetrical Mode of DNA Replication"; The Journal of Biological Chemistry, vol. 264, No. 15, Issue of May 25, pp. 8935-8940, 1989.
Picher, Angel J. et al. "TruePrime is a novel method for whole-genome amplification from single cells based on TthPrimPol," Nature Communications, 16 pages; Nov. 29, 2016.
European Patent Office, Examination Report for EP 20730981.6 dated May 4, 2023, 4 pages.
International Search Report and Written Opinion for PCT/EP2020/063740 dated Aug. 31, 2020, 14 pages.
Decision of Rejection (English Translation) for JP 2021-568525 dated Dec. 9, 2024, 4 pages.
Written Opinion for SG 11202112620T dated Sep. 23, 2024, 6 pages.
Examination Report for AU 2020277641 dated Jul. 2, 2025, 4 pages.
Office Action (English Translation) for CN 202080036838.X dated Apr. 11, 2025, 4 pages.

(Continued)

*Primary Examiner* — Jennifer M.H. Tichy
*Assistant Examiner* — Emily F Eix
(74) *Attorney, Agent, or Firm* — Brian E. Davy; Bozicevic, Field & Francis LLP

(57) ABSTRACT

Disclosed herein are mutants of bacteriophage Phi29 DNA polymerase with improved primer recognition, compared to the wild-type enzyme. Certain mutants comprise one or both of the mutations K64R or M97K. The provided mutants are capable of using more efficiently shorter and longer random synthetic DNA primers than wild-type Phi29 DNA polymerase, generating more amplification product in Multiple Displacement Amplification (MDA) reactions. The inventive mutants amplify human genomic DNA with less bias and better coverage in comparison to reactions carried out with wild-type Phi29 DNA polymerase.

15 Claims, 17 Drawing Sheets

Specification includes a Sequence Listing.

(56)     References Cited

OTHER PUBLICATIONS

Notice of Grounds for Rejection (English Translation) for KR
10-2021-7040028 dated Sep. 29, 2025, 5 pages.
Office Action for Application No. CA 3,140,244 dated Oct. 10,
2025, 4 pages.

* cited by examiner

WT ▦ K64R ▦ M97K ▦ K64R/M97K

5N

Low

High

PHI29 DNA POLYMERASE MUTANTS WITH IMPROVED PRIMER RECOGNITION

REFERENCE TO RELATED APPLICATIONS

This application claims the benefit of the priority date of U.S. Provisional Application 62/849,252, filed May 17, 2019, the contents of which are incorporated herein in their entirely.

SEQUENCE LISTING

This application contains a Sequence Listing in computer readable form, which is incorporated herein by reference.

BACKGROUND

Phi29 DNA polymerase (Phi29 DNApol) is a monomeric enzyme (66 kDa) in charge of replicating the bacteriophage genome (19285 bp) by catalyzing both protein-primed initiation at both ends of the linear dsDNA molecule, and full elongation of each DNA strand (Blanco and Salas, 1984; 1985). Phi29 DNApol belongs to family B of DNA polymerases (Bernad et al, 1987), showing the common right-hand fold containing the palm, thumb and finger subdomains, but also two additional domains called TPR1 and TPR2 (Rodriguez et al, 2005; Kamtekar et al, 2006; Berman et al, 2007). Phi29 DNApol shows unique properties that enable its application in numerous DNA amplification and DNA sequencing technologies and platforms: highly processive DNA synthesis, enabling the enzyme to incorporate more than 70000 nucleotides per DNA binding event in the absence of processivity factors (Blanco et al, 1989); exceptional strand-displacement, which allows polymerization coupled to the unwinding of double-stranded DNA, in the absence of helicase-type enzymes (Blanco et al, 1989); high fidelity of synthesis, with very low error insertion rates ($10^{-4}$ to $10^{-6}$) and efficient proofreading of inserted errors, which collectively enhance fidelity up to one error in $10^6$ to $10^8$ nucleotides incorporated (Esteban et al, 1993 and 1994).

These properties make Phi29 DNApol the best choice for isothermal multiple displacement amplification (MDA) (Dean et al, 2002) and rolling circle amplification (RCA) (Lizardi et al, 1998). These DNA amplification technologies are based on the combination of Phi29 DNApol with either random synthetic primers (RPs), mainly hexanucleotides or hexamers, or a DNA primase capable of synthesizing DNA primers in situ during the reaction (Picher et al, 2016).

Amplification of DNA is frequently required for the current sequencing technologies, since the amount of DNA available from certain samples (e.g., single cells) is not enough for the sequencing process. Unfortunately, DNA amplification has the risk of introducing errors, generating asymmetries (bias), and even promoting co-amplification of minute levels of contaminating DNA. Therefore, key parameters determining the quality of the amplification are the absence of contaminations and artefacts in the reaction products, coverage breadth and uniformity, low nucleotide error rates, and the ability to recover single nucleotide variants (SNVs), copy number variants (CNVs) and structural variants.

A source for potential amplification bias in the current MDA methods based on random hexamers is the priming inequality arising from different sequence-dependent hybridization kinetics of the oligonucleotides. Even more important is the propensity to generate primer-derived input-independent DNA amplification artefacts, caused by the exponential amplification of self-pairing hexamers.

It has been shown that the use of longer primers instead of hexamers with a reaction temperature of 40° C. decreases DNA amplification artefacts significantly (Alsmadi et al, 2009). The most likely reason behind this behavior is that the higher temperature reduces the likelihood of stable self-pairing of primers and therefore their subsequent amplification. However, to carry out the amplification reaction at a temperature as high as 40° C. (10° C. above the temperature optimum of Phi29 DNApol) thermostable or thermoresistant Phi29 DNApol variants are required. In this regard, some mutated Phi29 DNApols have been described to show improved thermostability (Povilaitis et al, 2016).

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

SUMMARY

Figure 1:
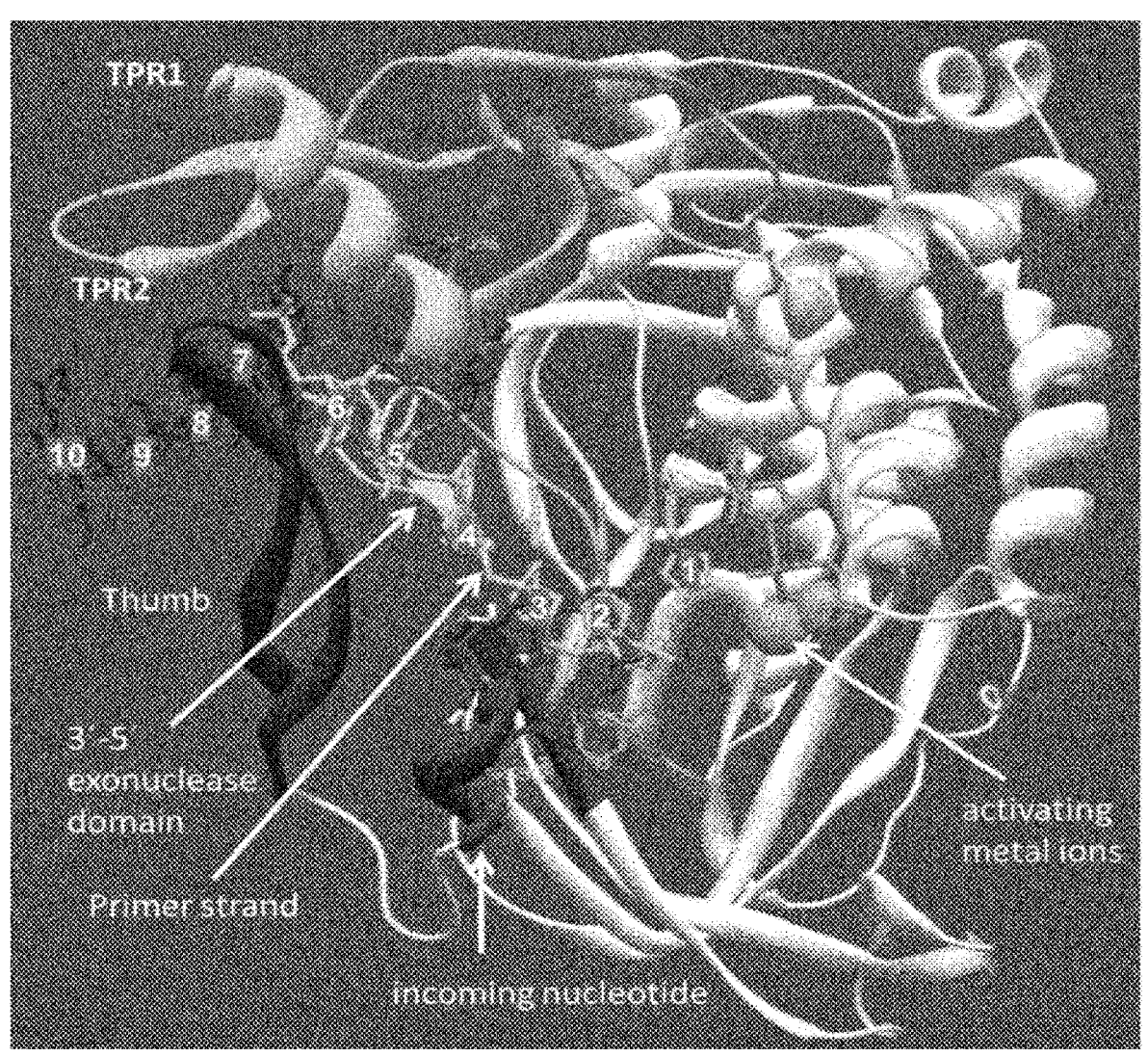
FIG. 1. 3D-structure of Phi29 DNApol complexed with DNA and dNTP (PDB id: 2PYL). Most of the protein is indicated in white, with the exception of THUMB (dark green), TPR2 (cyan) and TPR1 (yellow) subdomains. The N-terminal 3'-5' exonuclease domain is not fully depicted (only two segments are indicated (yellow), one containing $Arg^{96}$, and the other containing $Lys^{64}$). Primer strand (cyan), shows numbers corresponding to each nucleotide position. Template strand (light green), incoming nucleotide (magenta) and the two activating metal ions (beige) are also indicated.

Modified DNA polymerases can be useful in multiple applications like DNA sequencing, DNA amplification, library preparation, DNA genotyping, etc. The present invention provides recombinant Phi29 DNA polymerases including mutations that confer improved properties, particularly desirable for these or other applications. These amino acid sequence changes can improve performance in multiple displacement DNA amplification (MDA) by using shorter random synthetic primers, which results in reduced amplification artefacts, better sequence-dependent hybridization kinetics, and therefore, resulting in an improved coverage breadth and uniformity. "Phi29" is sometimes written "φ29".

The recombinant Phi29 DNA polymerase comprises one or two mutations from the group consisting of K64R and M97K.

DETAILED DESCRIPTION

I. Definitions

"Isolated" means a molecule is the predominant species present, i.e., on a molar basis, more abundant than any other individual macromolecular species in the composition. Generally, an isolated molecule can comprise more than 80%, more than 90%, more than 95%, more than 98%, or more than 99% of the macromolecular species present in the composition is the purified species of interest. Solvent species, small molecules (<500 Daltons), stabilizers (e.g., BSA), and elemental ion species are not considered macromolecular species for purposes of this definition.

As used herein, the term "recombinant nucleic acid" refers nucleic acid molecule comprising two or more attached nucleotide sequences not normally attached to each other in nature.

As used herein, the term "recombinant cell" refers to a cell, e.g., an animal, plant, fungal or microbial (e.g., bacterial) cell, that comprises a recombinant nucleic acid.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

A "reference sequence" is a defined sequence used as a basis for a sequence comparison and may be a subset of a larger sequence, e.g., a complete cDNA, protein, or gene sequence.

Because two nucleic acids or polypeptides each may comprise (1) a sequence (i.e., only a portion of the complete nucleic acid or polypeptide sequence) that is similar between the two nucleic acids, or (2) a sequence that is divergent between the two nucleic acids, sequence comparisons between two (or more) nucleic acids or polypeptides are typically performed by comparing sequences of the two nucleic acids over a "comparison window" to identify and compare local regions of sequence similarity.

A "comparison window" refers to a conceptual segment of typically at least 12 consecutive nucleotides or 4 consecutive amino acid residues that is compared to a reference sequence. The comparison window frequently has a length of at least 15 or at least 25 nucleotides or at least 5 or at least 8 amino acids. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, WI) or by inspection, and the best alignment (i.e., resulting in the highest percentage of homology over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the num- [5] ber of positions at which the identical nucleotide or amino acid occurs in both sequences to yield the number of matched positions, dividing the number of matched positions by the total number of positions in the window of comparison (i.e., the window size), and multiplying the [10] result by 100 to yield the percentage of sequence identity.

Unless otherwise specified, the comparison window used to compare two sequences is the length of the shorter sequence.

Methods are described further in Natl. Acad. Sci. USA [15] 85:2444; Higgins & Sharp (1988) Gene 73:237-244; Higgins & Sharp, CABIOS 5:151-153 (1989); Corpet et al. (1988) Nucleic Acids Research 16:10881-90; Huang et al. (1992) Computer Applications in the Biosciences 8:155-65; and Pearson et al. (1994) Methods in Molecular Biology [20] 24:307-31. Alignment is also often performed by inspection and manual alignment.

A subject nucleotide sequence or amino acid sequence is "substantially identical" to a reference sequence if the subject amino acid sequence or nucleotide sequence has at [25] least 80% sequence identity over a comparison window. Thus, sequences that have at least 85% sequence identity, at least 90% sequence identity, at least 95% sequence identity, at least 98% sequence identity or at least 99% sequence identity with the reference sequence are also "substantially [30] identical". Two sequences that are identical to each other are, of course, also "substantially identical".

As used herein, the term "transcription regulatory sequence" refers to a first nucleotide sequence that regulates transcription of a second nucleotide sequence to which it is [35] operatively linked.

As used herein, a nucleotide sequence is "operatively linked" with a transcription regulatory sequence when the transcription regulatory sequence functions in a cell to regulate transcription of the nucleotide sequence. This [40] includes promoting transcription of the nucleotide sequence through an interaction between a polymerase and a promoter.

A "promoter" is a transcription regulatory sequence at least sufficient to promote the transcription of a nucleotide [45] sequence in DNA into an RNA transcript. A transcript transcribed from a promoter typically includes sequences from the promoter downstream of the transcription start site, as well as downstream sequences that, in the case of mRNA, encode an amino acid sequence. Promoters are the best- [50] characterized transcriptional regulatory sequences because of their predictable location immediately upstream of transcription start sites. Promoters include sequences that modulate the recognition, binding and transcription initiation activity of the RNA polymerase. These sequences can be cis [55] acting or can be responsive to trans acting factors. Promoters, depending upon the nature of the regulation, can be constitutive or regulated. They are often described as having two separate segments: core and extended promoter regions.

The core promoter includes sequences that are sufficient [60] for RNA polymerase recognition, binding and transcription initiation. The core promoter includes the transcriptional start site, an RNA polymerase binding site, and other general transcription binding sites and is where the pre-initiation complex forms and the general transcription machinery [65] assembles. The pre-initiation complex is generally within 50 nucleotides (nt) of the transcription start site (TSS).

The core promoter also includes a sequence for a ribosome binding site, necessary for translation of an mRNA into a polypeptide.

The extended promoter region includes the so-called proximal promoter, which extends to about 250 nucleotides upstream of the transcriptional start site (i.e., −250 nt). It includes primary regulatory elements such as specific transcription factor binding sites. It has been found that many genes have transcription regulatory elements located further up-stream. In particular, a fragment that includes most of the transcription regulatory elements of a gene can extend up to 700 nt or more up-stream of the transcription start site. In certain genes, transcription regulatory sequences have been found thousands of nucleotides upstream of the transcriptional start site.

As used herein, a first nucleotide sequence is "heterologous" to a second nucleotide sequence if the first nucleotide sequence is not attached, e.g., operatively linked, with the second nucleotide sequence in nature. By extension, a polypeptide is "heterologous" to transcription regulatory sequence if it is encoded by a nucleotide sequence heterologous the transcription regulatory sequence.

As used herein, the term "allelic variant" refers to a naturally occurring variation of a gene.

As used herein, the term "artificial variant" refers to a gene or protein comprising one or more genetic modifications to a naturally occurring gene or protein.

As used herein, the term "mutation" as used herein, generally refers to an alteration, variant or polymorphism in a nucleotide sequence compared with wildtype. Such alteration, variant or polymorphism can be with respect to a reference genome, eg., in a genomic database. Mutations include, without limitation, single nucleotide variations (SNVs), substitutions, insertions or deletions (also referred to collectively as "indels"), and repeats.

II. Introduction

A novel strategy to reduce amplification artefacts and amplification biases derived from sequence-dependent hybridization kinetics could take advantage of using DNA primers shorter than the current gold-standard hexamers. That strategy, which requires obtaining Phi29 DNApol variants able to recognize, stably bind and efficiently use shorter DNA primers, would allow to improve current DNA amplification technologies significantly.

The availability of the 3D-structure of Phi29 DNApol complexed with DNA and incoming nucleotide (Berman et al, 2007) allowed us to perform a detailed inspection of the amino acid residues directly involved in interactions with the primer strand (FIG. 1). These ligands of the primer strand (see the scheme at FIG. 2A) are:

R96 (interacts with the phosphodiester between nucleotide 7 and 8 of the primer).

R306 (interacts with the phosphodiester between nucleotide 8 and 9 of the primer).

R308 (interacts with the phosphodiester between nucleotide 9 and 10 of the primer).

K498 (interacts with the sugar of the first 3' nucleotide of the primer).

Y500 (interacts with the phosphodiester between nucleotide 1 and 2 of the primer).

K529 (interacts with the phosphodiester between nucleotide 1 and 2 of the primer).

Based on these few contacts, Phi29 DNApol establishes direct interactions which span the first 10 bases of the primer strand, suggesting that such a size would confer the maximal binding stability to the primer. It is quite surprising that there is a lack of contacts in the interval between nucleotides 3 and 6. Strikingly, current MDA procedures with Phi29 DNApol are based on the provision of random hexamers, which will be poorly stabilized just by contacts with the phosphodiester bond between the two first nucleotides, and with the base of the 3'-terminal nucleotide. Therefore, hexamers do not have an optimal size to be used as initial primers to be bound and extended by Phi29 DNApol. Very likely, these sub-optimal primers were selected to have complements in any DNA sample at sufficiently short intervals to enable efficient and even amplification, while minimizing self-hybridization artefacts, known as primer-dimers.

On the other hand, the alternative TruePrime DNA amplification technology (Picher et al, 2016) takes advantage of a DNA primase (TthPrimPol) to synthesize the DNA primers on demand, but it has not been established which is the optimal primer size that is delivered by TthPrimPol to Phi29 DNApol, and what is the fate of those primers that remain shorter than the minimum size required for optimal elongation by Phi29 DNApol.

Based on this information and caveats, we explored the possibility of generating Phi29 DNApol mutants (inventive variants) with an improved affinity for short primers, ideally in the limit between 4 and 6 nucleotides. For this purpose, we followed two different approaches: 1) reinforcing some existing interactions, 2) creating new (non-existing) enzyme:DNA ligands in the primer region.

Such an improved variants are expected to be valuable in RPs-based MDA procedures, likely reducing primer-dimer artefacts, and the formation of amplification chimeras. Additionally, in the context of the TruePrime DNA amplification technology, the use of short primers that could be generated by TthPrimPol, could increase the efficiency of amplification, and/or lead to an improved coverage.

Again, a detailed analysis of the 3D-structure of Phi29 DNApol (Berman et al, 2007) allowed the selection of 5 amino acid residues as candidates for a "gain of function" mutations. These residues are: Lys64 (located at ExoII motif), Met97 (neighbor to Arg96, a primer ligand of WT Phi29 DNApol), Thr499 (neighbor to Lys498 and Tyr500, two primer ligands of WT Phi29 DNApol), Thr534 and Lys538 (close to Lys529, a primer ligand of WT Phi29 DNApol). The mutations selected at these residues (summarized in FIG. 2B) were:

K64R, producing the gain of interaction with the phosphodiester between residues 4 and 5 of the primer strand.

K64KG; K64KK; L63LG; L63LH, as +1 insertion mutations flanking Lys64, designed in agreement with the heterogeneity observed at different ExoII motifs of B family DNA polymerases. These changes are also predicted to gain interaction with residues 4 and 5 of the primer strand.

R96K, predicted to weaken the interaction with the phosphodiester bond between residues 7 and 8 of the primer.

M97K, producing the gain of interaction with the nitrogen base of the nucleotide 5 of the primer strand.

M97R, producing the gain of interaction with the bases of the amino acid residues 4 and 5 of the primer strand.

T499K, producing the gain of interaction with the sugar of the amino acid residue 5 of the template strand.

T499R, producing the gain of interaction with the sugar of the amino acid residues 4 and 5 of the template strand.

K529R, producing the gain of a double interaction with the phosphodiester bonds between residues 1 and 3 of the primer strand.

T534K, producing the gain of interaction with the sugar of the amino acid residue 4 of the primer strand.

T534R, producing the gain of interaction with the phosphodiester between residues 3 and 4 of the primer strand.

K538R, producing the gain of interaction with the phosphodiester between residues 2 and 3 of the primer strand.

The indicated mutants, designed to increase the affinity of Phi29 DNApol for short primers, were expressed and purified following standard protocols to obtain WT Phi29 DNApol. It cannot be predicted if any particular gain of interaction with the primer strand originated by the mutations introduced will have an adverse effect on Phi29 DNApol features as translocation, processivity, or the appropriate (TthPrimPol) and randomly-primed DNA amplification technologies.

III. Nucleic Acids, Expression Constructs, Recombinant Cells and Mutant Polymerase Polypeptides A. Nucleic Acids Provided herein are nucleic acids having nucleotide sequences that encode mutant Phi29 polymerases with improved primer recognition. Nucleotide sequence for a wild type Phi29 polymerase is provided in SEQ ID NO.: 1. Nucleic acids encoding mutant Phi29 polymerases sequences encoding have one or both mutations K64R and M97K. In some embodiments nucleotide sequences encoding one or both of these mutations are substantially identical to the sequence of SEQ ID NO.: 1.

B. Expression Constructs

Also provided herein are expression constructs comprising a transcription regulatory sequence operatively linked to a nucleotide sequence encoding a mutant Phi29 polymerase as described herein. The expression construct can take the form of a plasmid or any other form appropriate for expression in a cell of interest.

C. Recombinant Cells

Also provided herein are recombinant cells comprising an expression construct as described herein. In certain embodiments the cells are bacterial cells. Such recombinant cells are useful for reproducing the nucleic acid molecules of this disclosure and for producing mutant Phi29 polymerases of this disclosure. Mutant Phi29 polymerases can be produced by culturing recombinant cells comprising an expression construct. The transcription regulatory sequence used can comprise a constitutive promoter.

D. Mutant Phi29 Polymerases

Also provided herein are mutant Phi29 polymerases with improved primer recognition. The mutant Phi29 polymerases of this disclosure have amino acid sequences that are substantially identical to the amino acid sequence of SEQ ID NO: 1 (also deposited as UniProtKB—P03680) and that comprise one or both amino acid substitutions K64R and M97K.

Polymerases having substantially identical amino acid sequences can be based on naturally occurring sequences, such as allelic variants, provided they include one or both of the amino acid substitutions K64R and M97K. Such variants can have at most or no more than any of 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions, additions or deletions compared with the wild type sequence SEQ ID NO.: 1, again provided that one or both of amino acid substitutions K64R and M97K are present.

Preferably, the amino acid sequence of the DNA polymerases of the invention have an identity of at least 80% with SEQ ID NO: 2, SEQ ID NO: 3 or SEQ ID NO: 4. More preferably, the amino acid sequence of polymerases of the invention have an identity of at least 90% with SEQ ID NO: 2, SEQ ID NO: 3 or SEQ ID NO: 4. Still more preferably, the amino acid sequence of polymerases of the invention is SEQ ID NO: 2, SEQ ID NO: 3 or SEQ ID NO: 4.

IV. Methods of Use

Provided herein are methods of performing primer extension and/or nucleic acid polymerization using the mutant Phi29 polymerases described herein. Methods of primer extension are useful in nucleic acid replication, amplification and sequencing.

Primer extension involves hybridization of a primer to a nucleic acid molecule template followed by a polymerization reaction catalyzed by a polymerase that adds nucleotides to the 3' terminus of the primer. Primers can be added to the reaction mixture exogenously, or can be produced by a primase/polymerase. Primases are enzymes that catalyzes the synthesis of an oligonucleotide, called a primer, complementary to a nucleic acid template. One such primase is such as TthPrimPol.

Synthetic primers are typically used in nucleic acid amplification. Such primers typically are between about six and about 25 nucleotides in length. When specific sequences are to be amplified, primers can have sequences complementary to the target sequence. For purposes of whole genome amplification or other nondirected amplification methodologies, random primers can be used. Random primers typically comprise a collection or set of oligonucleotides in which each of the bases is present at each position in the oligonucleotide in one or more of the primers in the set. In certain situations, one or more of the positions (e.g., 1, 2, 3, 4, 5, 6, 7, 8, 9, or 10) can be filled by a fixed base or a combination of two or three bases.

A. Amplification

Amplification of nucleic acids, for example by polymerase chain reaction (PCR) as introduced by Mullis (U.S. Pat. No. 5,656,493) is an indispensable technique used in medical and biological research. It has been successfully used in a variety of applications like cloning, manipulating or sequencing of nucleic acids, DNA-based functional and phylogenetic analysis of genes, detection and diagnosis of diseases, as well as in forensic science and paternity testing.

B. Rolling Circle Amplification

Rolling circle amplification is a method of amplifying a covalently closed DNA molecule such as a single stranded, covalently closed DNA molecule. The template DNA molecule is primed with a primer, for example a primer provided by a primase/polymerase. A DNA polymerase performs primer extension on the primer around the closed DNA molecule. The polymerase displaces the hybridized copy and continues polynucleotide extension around the template to produce a concatenated amplification product.

C. Multiple Displacement Amplification (MDA)

Multiple displacement amplification (MDA) is an isothermal, non-PCR-based DNA amplification method in which priming and extension from a template produces ssDNA chains which can be continuously re-primed and copied by strand-displacement synthesis, producing a multi-branched DNA structure. After an initial denaturation of the double-stranded DNA sample, multiple strand displacement (MDA) amplification produces a multi-branched structure as DNA synthesis can be continuously primed and extended from many positions in the amplified molecules, without required further rounds of denaturation. Branches are displaced from each other as new primers are extended from one DNA molecule template into the branched area. MDA is further described in, for example, WO2011/047307A1, published Apr. 21, 2011 ("Multiple Displacement Amplification"). MDA could be described in brief as: isothermal polymerization that extends primers at multiple priming sites on self-generated ssDNA templates.

In certain embodiments MDA employs random trimers, tetramers, pentamers, hexamers, heptamers or octamers as primers to prime amplification at multiple sites on an initial template and amplified copies thereof. In certain embodiments of the disclosed methods, priming is accomplished with a DNA primase/polymerase, such as TthPrimPol.

In certain embodiments, amplification of double-stranded, linear polynucleotides involves using: 1) random synthetic primers and/or a DNA-directed primase/polymerase, such as TthPrimPol; 2) a modified DNA polymerase having strand-displacement activity, such as Phi29 DNApol; 3) dNTPs. In certain embodiments, the dNTP substrates are unmodified. In other embodiments, dNTPs can be modified by the attachment of a labeled group, for example, a fluorescent molecule. As used herein, the term "label" refers to a chemical moiety attached to a molecule, such as a nucleic acid molecule. Detectable labels include, for example, fluorescent labels, luminescent labels, enzymatic labels, colorimetric labels such as colloidal gold or colored glass or plastic beads and radioactive labels. In combination, these three reagents promote multiple displacement amplification (MDA) of a given DNA, multiply primed either by random synthetic primers or by the primase/polymerase and extended by the DNA polymerase. Furthermore, the combination of random synthetic primers and/or primase/polymerase and DNA polymerase can effect multiple strand displacement amplification through priming of amplified molecules with the primase/polymerase and/or random oligonucleotide primers and primer extension by the DNA polymerase.

1. DNA Polymerase with Strand Displacement Activity

Amplification methods as MDA can employ a DNA polymerase with strand displacement activity, e.g., a polymerase with strong binding to single-stranded DNA e.g., in preference to double-stranded DNA. Strand displacement activity can be useful in displacing hybridized strands of a DNA molecule while extending a primer position.

DNA polymerases with strand displacement activity useful in methods disclosed herein include, for example, Phi29 DNApol. Phi29 DNApol can be obtained commercially from, for example, New England Biolabs (Ipswich, MA, USA), ThermoFisher Scientific (Waltham, MA, USA and Expedeon (Cambridge, UK). Phi29 DNApol has both an intrinsic high processivity and strand-displacement ability coupled to DNA polymerization, being able to generate DNA fragments longer than 70 kb from a single enzyme: DNA binding event (Blanco et al., 1989). Such a potential enables Phi29 DNApol to replicate DNA templates containing secondary structures such as hairpin loops. The enzyme also has a 3'→5' exonuclease proofreading activity (Blanco and Salas, 1985; Garmendia et al., 1992) and provides up to 1000-fold higher fidelity compared to Taq DNA polymerase-based methods.

2. Deoxyribonucleoside Triphosphates

Primer creation and primer extension can be accomplished by the combination of a specialized DNA primase/polymerase as TthPrimPol, capable of synthesizing DNA primers (Picher et al, 2016), and a elongating DNA polymerase, as Phi29 DNApol, just by providing deoxyribo-nucleotide substrates e.g., dNTPs. Typically, these include the four standard bases, A, T, G and C. However, in certain embodiments non-natural nucleotides, such as inosine can be included. In certain embodiments nucleotides may bear a label for detection or capture of polynucleotides into which they are incorporated.

D. DNA Sequencing

As of today, a number of different sequencing techniques exist, that are commonly categorized under "first generation sequencing", "second generation sequencing" (often called "next generation sequencing" or NGS), and "third generation sequencing", also known as single molecule sequencing (SMS). First generation sequencing refers mainly to the methods of Maxam and Gilbert (Maxam and Gilbert, 1977) or Sanger (Sanger et al, 1977; Sanger and Coulson, 1978), of which only the latter is used today.

Second, or next generation sequencing refers to techniques that produce many sequences at the same time using advanced technical (optical) detection methods of base positions. An overview over existing methods is given in (Metzker, 2010).

Third generation or single molecule sequencing (SMS) techniques do not require prior amplification, and templates are not clones or ensembles of DNA, but single molecules whose sequence is often copied/read and online-recorded in "real time", as an outcome of the activity of a polymerase (Sam et al, 2011; Thompson and Milos, 2011).

As used herein, the term "high throughput sequencing" refers to the simultaneous or near simultaneous sequencing of thousands of nucleic acid molecules. Platforms for high throughput sequencing include, without limitation, massively parallel signature sequencing (MPSS), Polony sequencing, 454 pyrosequencing, Illumina (Solexa) sequencing, SOLiD sequencing, Ion Torrent semiconductor sequencing, DNA nanoball sequencing (Complete Genomics/BGI Shenzhen), Heliscope single molecule sequencing, single molecule real time (SMRT) sequencing (PacBio), and nanopore DNA sequencing (e.g., Oxford Nanopore).

Methods described herein can be used for, without limitation, whole genome sequencing, exome sequencing and amplicon sequencing. However, amplified molecules themselves, can be subject to amplification of specific amplicons. Sequence capture using baits directed to gene sequences in the genome can be used to isolate amplified molecules representing the exome. By reverse transcribing mRNA into double stranded cDNA an amplified transcriptome can be produced for sequencing.

V. Kits

Also provided herein are kits for use in performing the methods disclosed herein. As used herein, the term "kit" refers to a collection of items intended for use together.

Certain kits disclosed herein include 2, 3, 4, 5, 6, 7, elements selected from: (1) a PrimPol enzyme (e.g., TthPrimPol); (2) a DNA polymerase (e.g., Phi29 DNApol); (3) random trimers; (4) random tetramers; (5) random pentamers; (6) random heptamers; (7) random octamers; (8) random primers; (9) dNTPs; (10) reaction buffer; (11) a buffer for use with any of the aforementioned elements. Kits can include containers to hold reagents. Containers, themselves, can be placed into a shipping container. The container can be transmitted by hand delivery or by a common carrier, such as a national postal system or a delivery service such as FedEx. Kits also can contain a container for shipping collected blood to a central facility, such as a box or a bag.

Kits can also typically include instructions for use as well as and software for data analysis and interpretation.

Exemplary Embodiments

1. A Phi29 type DNA polymerase that comprises one or both of the mutations K64R or M97K.

2. A Phi29 type DNA polymerase that has an amino acid sequence having an identity of at least 80% with SEQ ID NO: 2; SEQ ID NO. 3 or SEQ ID NO 4.

3. A method for replicating, amplifying or sequencing a template DNA which comprises contacting said DNA with a reaction mixture comprising at least: a) the DNA polymerase according to any of embodiments 1 to 2, b) a buffer, c) magnesium chloride, d) a primer, and e) nucleoside triphosphates. 4. A kit for carrying out a method according to embodiment 3 comprising: a) the DNA polymerase according to any of embodiments 1 to 2, b) a buffer, and c) magnesium chloride.

5. A kit for carrying out a method according to embodiment 3 comprising the DNA polymerase according to any of embodiments 1 to 2, and one or more of: (a) a PrimPol enzyme (e.g., TthPrimPol); (b) random trimers; (c) random tetramers; (d) random pentamers; (e) random heptamers; (f) random octamers; (g) dNTPs; (h) reaction buffer; (i) a buffer for use with any of the aforementioned elements.

6. A Phi29 type DNA polymerase, wherein the Phi29 type DNA polymerase has an amino acid sequence having at least 80%, 85%, 90%, 95%, 98% or 99% 99.5% sequence identity with SEQ ID NO:1, and wherein the Phi29 type DNA polymerase comprises one or both amino acid substitutions K64R and M97K. 7. The Phi29 type DNA polymerase of embodiment 6, having a sequence of SEQ ID NO:2, SEQ ID NO:3, or SEQ ID NO:4. 8. The Phi29 type DNA polymerase of embodiment 6, having no more than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions, additions or deletions in addition to one or both of amino acid substitutions K64R and M97K.

9. An isolated nucleic acid molecule comprising a nucleotide sequence encoding a Phi29 type DNA polymerase, wherein the Phi29 type DNA polymerase has an amino acid sequence having at least 80%, 85%, 90%, 95%, 98% or 99% 99.5% sequence identity with SEQ ID NO:1, and wherein the Phi29 type DNA polymerase comprises one or both amino acid substitutions K64R and M97K. 10. The isolated nucleic acid molecule of embodiment 9, wherein the Phi29 type DNA polymerase has a sequence of SEQ ID NO:2, SEQ ID NO:3, or SEQ ID NO:4. 11. The isolated nucleic acid molecule of embodiment 9, wherein the Phi29 type DNA polymerase has no more than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions, additions or deletions in addition to one or both of amino acid substitutions K64R and M97K. 12. A recombinant nucleic acid comprising an transcription regulatory sequence operatively linked with a Phi29 type DNA polymerase of any of embodiments 9-11. 13. The recombinant nucleic acid of embodiment 12, wherein the transcription regulatory sequence comprises a bacterial or mammalian promoter. 14. The recombinant nucleic acid of embodiment 12 contained in a vector selected from a plasmid vector, a viral vector, a cosmid, and a transposon. 15. The recombinant nucleic acid of embodiment 14, comprising a cloning site positioned relative to the nucleotide sequence encoding the Phi29 type DNA polymerase such that an transcription regulatory sequence inserted into the cloning site becomes operatively linked with the nucleotide sequence encoding the Phi29 type DNA polymerase.

16. A recombinant cell comprising a recombinant nucleic acid of any of embodiments 12-15.

17. A method comprising: a) contacting a nucleic acid template molecule with a Phi29 type DNA polymerase of any of embodiments 1, 2, 6-8, and reagents sufficient for primer extension; and b) performing primer extension with the polymerase using the nucleic acid template.

18. The method of embodiment 17, wherein the reagents sufficient for primer extension comprise oligonucleotide primers.

19. The method of embodiment 18, wherein the oligonucleotide primers comprise one or more of trimers, tetramers, pentamers, hexamers, hexamers, octomers, nonamers or 10-mers.

20. The method of embodiment 19, wherein the primers are random primers.

21. The method of embodiment 18, wherein the oligonucleotide primers have links between five and 25 nucleotides.

22. The method of embodiment 17, wherein the reagents sufficient for primer extension comprise a primase/polymerase (e.g., TthPrimPol).

23. The method of embodiment 17, wherein primer extension is performed at a temperature about, or above, any of 31° C., 32° C., 33° C., 34° C., 35° C., 36° C., 37° C., 38° C., 39° C., 40° C., 41° C., or 42° C.

24. The method of embodiment 17, wherein the template nucleic acid molecule is present in an amount no greater than 1 ng, 100 pg, 10 pg, or 1 pg.

25. The method of embodiment 17, wherein the primer extension comprises (i) multiple displacement amplification ("MDA") or (2) rolling circle amplification.

26. The method of embodiment 17, wherein the primer extension comprises multiple annealing and looping-based amplification cycles (MALBAC).

27. The method of any of embodiments 17-26, wherein the Phi29 type DNA polymerase comprises both of substitutions K64R and M97K.

EXAMPLES

Example 1: Screening to Detect which Mutants are Able to Use Shorter Random Synthetic Primers than WT Phi29 DNA Pol in Multiple Displacement Amplification Reactions Shown in FIG. 3 is the amplification of 1 ng of human genomic DNA by multiple displacement amplification (MDA) combining Phi29 DNApol variants and TthPrimPol or random synthetic primers of different sizes: trimers (3N), tetramers (4N), pentamers (5N), hexamers (6N), heptamers (7N) or octamers (8N).

Figure 3:
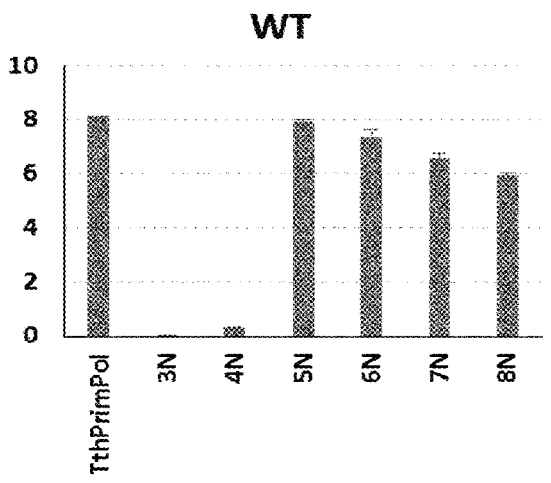
FIG. 3. Amplification efficiency of WT Phi29 DNApol or the designed mutants, in combination with TthPrimPol or random primers of different lengths: trimers (3N), tetramers (4N), pentamers (5N), hexamers (6N), heptamers (7N) or octamers (8N), using 1 ng of human genomic DNA as input in the reaction.
Figure 3:
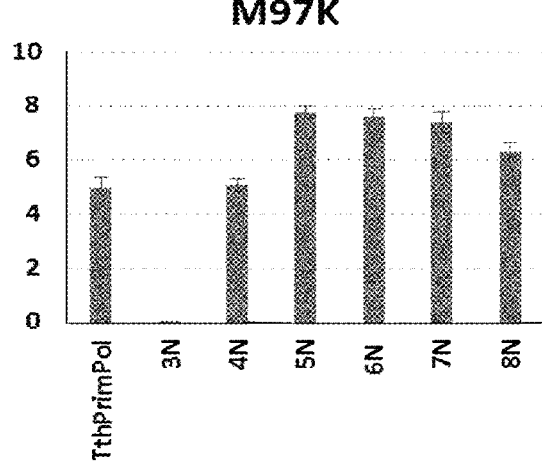
Figure 3:
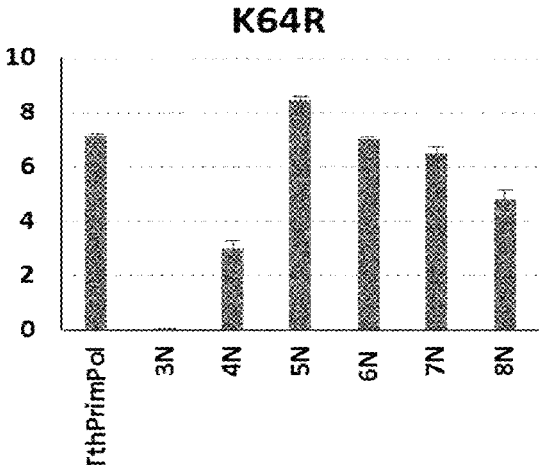
Figure 3:
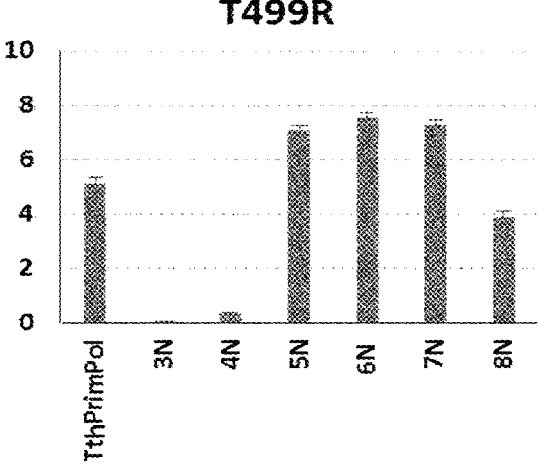
Figure 3:
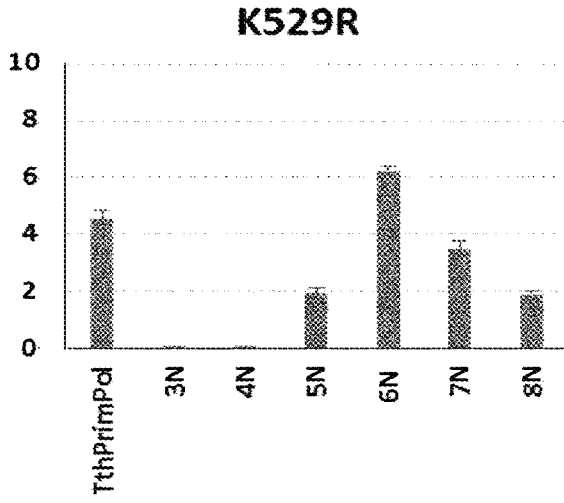
Figure 3:
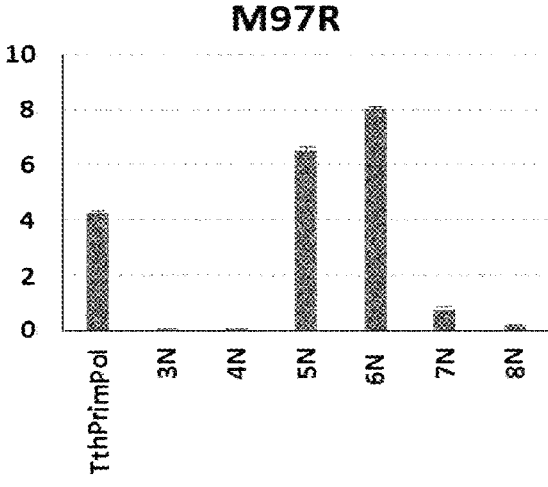
Figure 3:
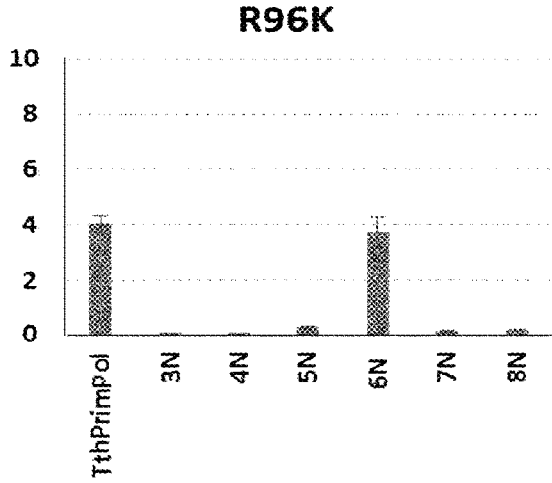
Figure 3:
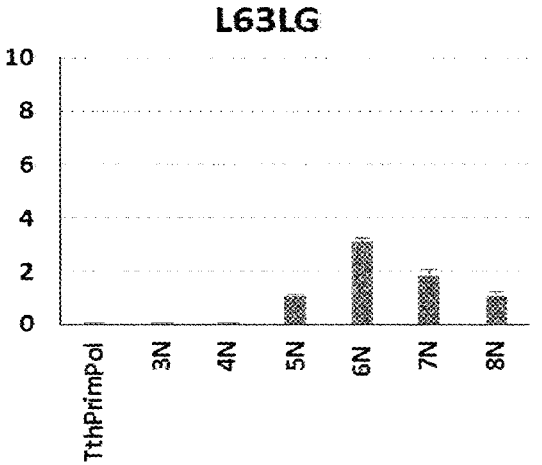
Figure 3:
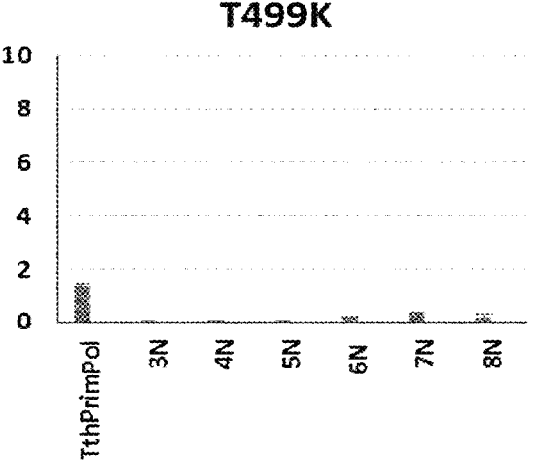
Figure 3:
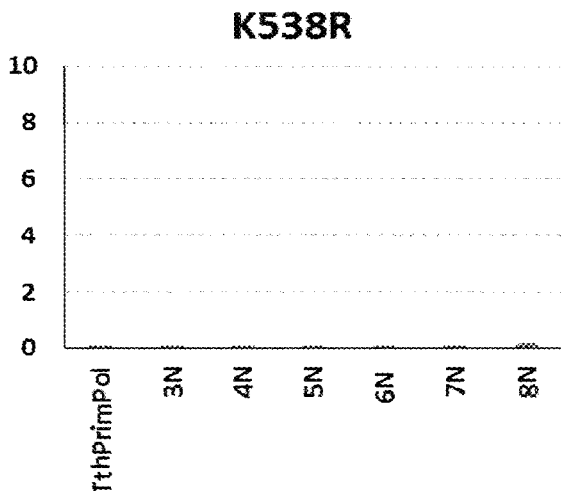
Figure 3:
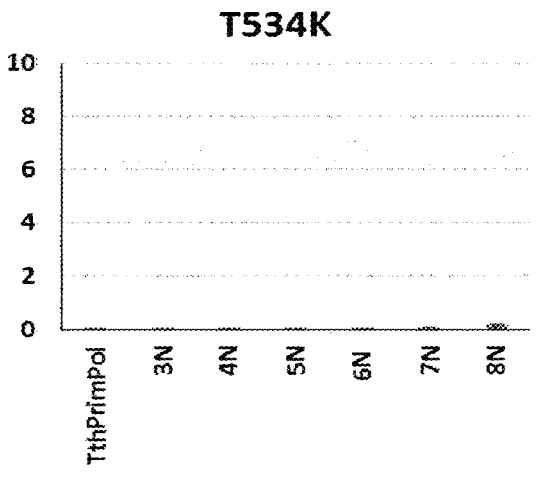
Figure 3:
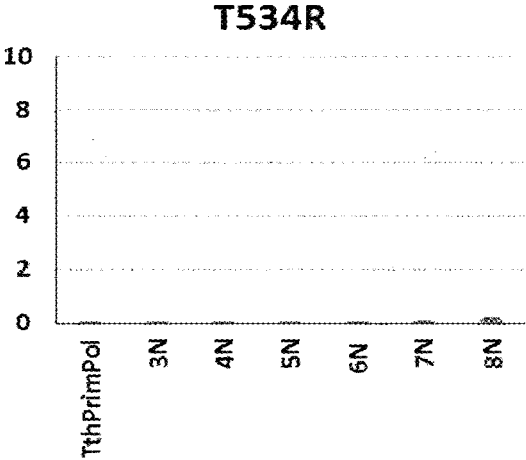
Figure 3:
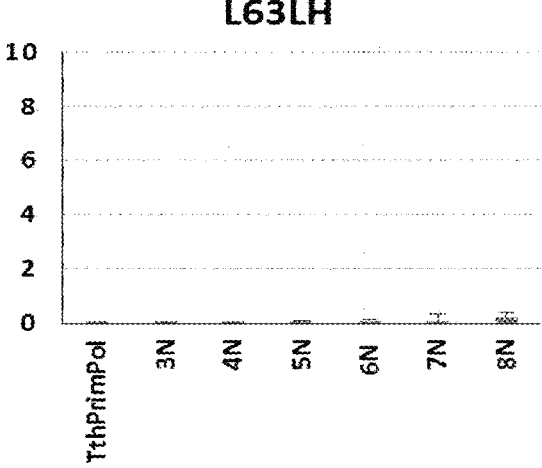
Figure 3:
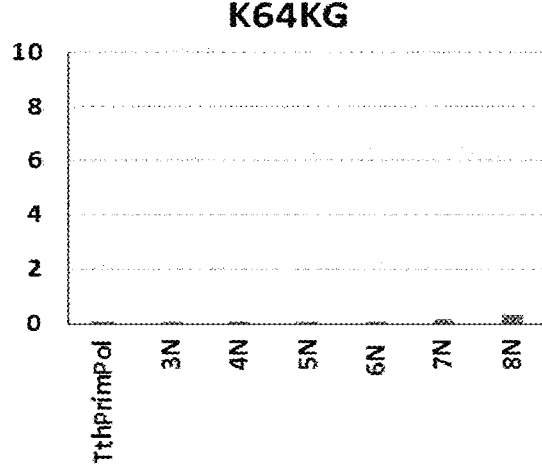
Figure 3:
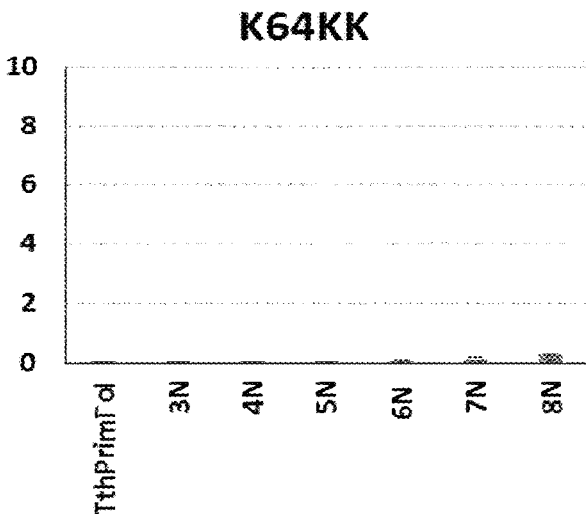

As observed in FIG. 3, WT Phi29 DNApol efficiently used pentamers, hexamers, heptamers and octamers, as well as TthPrimPol, to amplify human genomic DNA. Trimers and tetramers were not suitable to carry out the amplification.

From the group of Phi29 DNApol variants generated, six of them (K538R, T534K, T534R, L63LH, K64KG and K64KK) were completely inactive in MDA independently of the primer size or the alternative use of TthPrimPol. Another set of mutants (K529R, M97R, R96K, L63LG and T499K) revealed worse amplification performance than WT Phi29 DNApol, showing lower amplification yields and/or limitations to use certain primer sizes. For example, mutant M97R was able to use pentamers and hexamers efficiently, while heptamers and octamers did not trigger the amplification. Similarly, mutant R96K was only able to use hexamers from the set of random synthetic primers. Strikingly, insertion mutant L63LG was able to amplify the DNA with pentamers, hexamers, heptamers and octamers, but the combination with TthPrimPol did not produce any amplified material. On the contrary, mutant T499K was only able to slightly amplify the DNA in the presence of TthPrimPol, while none of the random synthetic primers promoted MDA.

Mutant T499R showed a behavior approximately similar to WT Phi29 DNApol.

Finally, mutants K64R and M97K showed significant improvements with respect to WT Phi29 DNApol. Both of them were the only ones able to use tetramers, while WT Phi29 DNApol and the rest of the mutants did not show any amplification yield.

The two "gain of function" mutations were introduced into the same polypeptide to generate the double mutant K64R/M97K, which was deeply characterized in comparison to WT Phi29 DNApol and single mutants K64R and M97K, as it is shown in the following examples.

Figure 4:
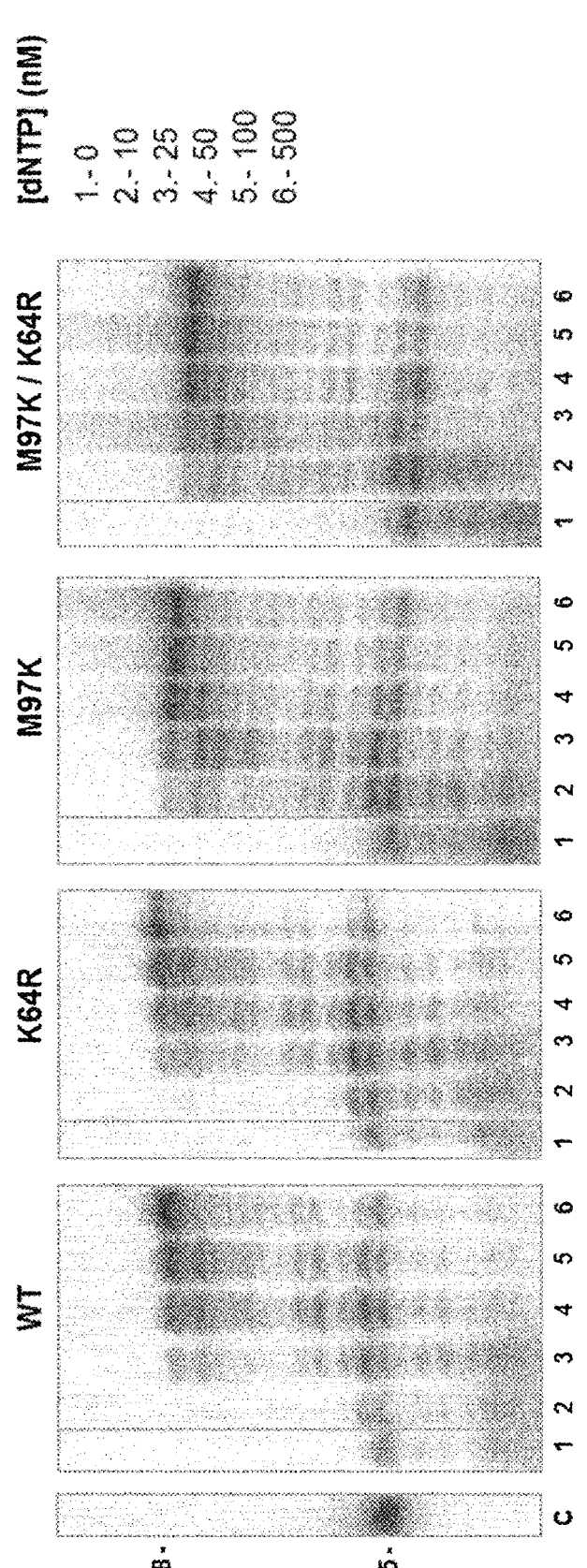
FIG. 4. Balance of exonuclease and polymerase activities of WT Phi29 DNApol, mutant K64R, mutant M97K and double mutant K64R/M97K, as a function of the deoxynucleotides (dNTP) concentration provided.

Example 2: Polymerase Activity is Favored Versus Exonuclease Activity in Phi29 DNApol Mutant M97K and Double Mutant K64R/M97K Shown in FIG. 4 is the analysis of the dynamic equilibrium between 3'-5' exonuclease and 5'-3' polymerization activities of the most relevant inventive mutants with respect to the WT Phi29 DNApol (K64R, M97K and double mutant K64R/M97K). A DNA duplex formed by a 5'-labelled primer (5' GATCACAGTGAGTAC, SEQ ID NO: 5) hybridized to a template (5' AGAAGTGTATCTGGTACT-CACTGTGATC, SEQ ID NO: 6) was used to analyze the coupling between DNA synthesis and DNA degradation as a function of dNTP concentration (0, 10, 25, 50 100 and 500 nM). In the absence of dNTPs, the exonucleolytic degradation of the primer-terminus is observed. The degradation pattern reflects the level of exonuclease activity of the inventive variants with respect to the WT Phi29 DNApol. As the concentration of dNTPs increases, the exonuclease activity is progressively overcome by the 5'-3' polymerization and net dNMP incorporation can be observed as an increase in the size of the labelled primer, defining the concentration of dNTPs needed to obtain an efficient elongation of the primer for each mutant. As observed in FIG. 4, mutant K64R showed a Pol/Exo equilibrium approximately similar to that displayed by the WT enzyme, reaching the 28-mer position at 25 nM dNTPs. On the other hand, mutant M97K and double mutant K64R/M97K reached the same position (28-mer) with the lowest dNTP concentration tested (10 nM), indicating that the polymerase activity of these mutants is favored versus exonuclease.

Example 3: The Inventive Mutants (K64R, M97K and K64R/M97K) are Able to Use Shorter Random Synthetic Primers than WT Phi29 DNApol in Multiple Displacement Amplification Reactions Shown in FIG. 5 is the amplification of 1 ng of human genomic DNA by multiple displacement amplification combining Phi29 DNApol selected variants (K64R, M97K and double mutant K64R/M97K) and random synthetic primers of different sizes: trimers (3N), tetramers (4N), pentamers (5N), hexamers (6N), heptamers (7N) or octamers (8N).

Amplification yields shown are the mean of two independent experiments that included 3 replicates per condition each. Standard deviation from the two experiments is depicted.

Figure 5:
FIG. 5. Amplification efficiency of WT Phi29 DNApol, mutant K64R, mutant M97K and double mutant K64R/M97K, in combination with random primers of different lengths: trimers (3N), tetramers (4N), pentamers (5N), hexamers (6N), heptamers (7N) or octamers (8N), using 1 ng of human genomic DNA as input in the reaction. For each primer length N the columns are shown in the following order from left to right: WT Phi29 DNApol, mutant K64R, mutant M97K double mutant K64R/M97K.

As observed in FIG. 5, none of the enzymes tested were able to efficiently amplify genomic DNA using random synthetic trimers. Only the double mutant K64R/M97K showed a yield close to 1 μg.

The three inventive variants were able to use tetramers to trigger the amplification, while no amplification was observed with the WT Phi29 DNApol. Variant K64R showed the lowest amplification yield (2.7 μg), mutant M97K displayed a slightly higher yield (3.8 μg), and double mutant K64R/M97K exhibited a much higher yield (12.9 μg). The highest yield observed in the double mutant indicates synergic effects of both mutations in the same polypeptide.

The WT Phi29 DNApol and the three inventive variants were able to use random pentamers efficiently to start off the amplification. Again, the double mutant K64R/M97K produced the highest yield, more than 20 μg of amplified DNA, clearly overcoming the performance of single variants and WT enzyme.

In the case of random hexamers, a similar comparative pattern is observed, although the amplification yields are higher in all cases.

Using random heptamers, WT Phi29 DNApol kept the same yield with respect to the results obtained using hexamers, while the three inventive variants tended to decrease the amplification efficiency, producing DNA levels similar to those obtained with random pentamers.

In the case of octamers, both K64R and M97K single mutants showed amplification yields lower than the WT Phi29 DNApol. On the other hand, double mutant K64R/M97K clearly overcame the WT Phi29 DNApol, as it occurred in all conditions tested, confirming robust and efficient amplification values independently of the length of the random synthetic primer used to initiate the amplification.

Example 4: Effect of Ionic Strength in the Background Amplification Observed in the Absence of Input DNA in Non-Template Controls (NTC)

Figure 6:
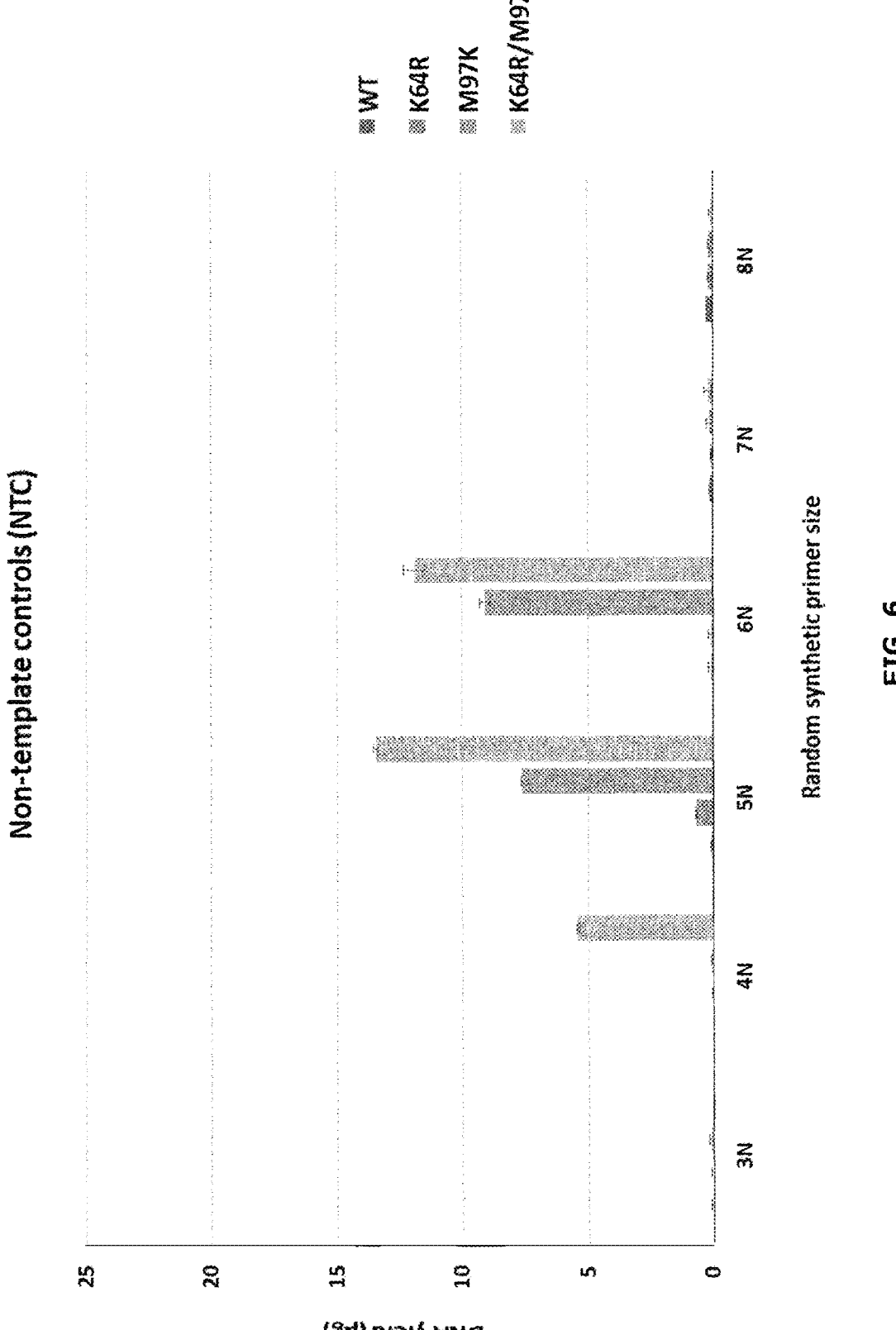
FIG. 6. Amplification yield observed in the absence of input DNA with either WT Phi29 DNApol, mutant K64R, mutant M97K or double mutant K64R/M97K, in combination with random synthetic primers of different sizes: trimers (3N), tetramers (4N), pentamers (5N), hexamers (6N), heptamers (7N) or octamers (8N), under low ionic strength conditions. For each primer length N the columns are shown in the following order from left to right: WT Phi29 DNApol, mutant K64R, mutant M97K double mutant K64R/M97K.

Shown in FIG. 6 is the amplification yields observed in the absence of input DNA when combining WT Phi29 DNApol or the selected inventive variants (K64R, M97K and K64R/M97K) and random synthetic primers of different sizes: trimers (3N), tetramers (4N), pentamers (5N), hexamers (6N), heptamers (7N) or octamers (8N).

Under the low ionic strength conditions tested (20 mM KCl; 57 mM NaCl), both M97K single mutant and K64R/M97K double mutant showed significant amplification yields in the absence of input DNA when using pentamers and hexamers, but also tetramers in the case of the double mutant (see FIG. 6). However, the amplification yields are significantly lower than the ones obtained when DNA (1 ng) is used as input in the same conditions (see FIG. 5), pointing to a different amplification mechanism involved. It is well-known in the field the primer-dimer amplification capacity of Phi29 DNApol in the absence of input DNA (Alsmadi et al, 2009), and the stability of primer-dimers may be enhanced in M97K single mutant and K64R/M97K double mutant under the conditions tested.

Figure 7:
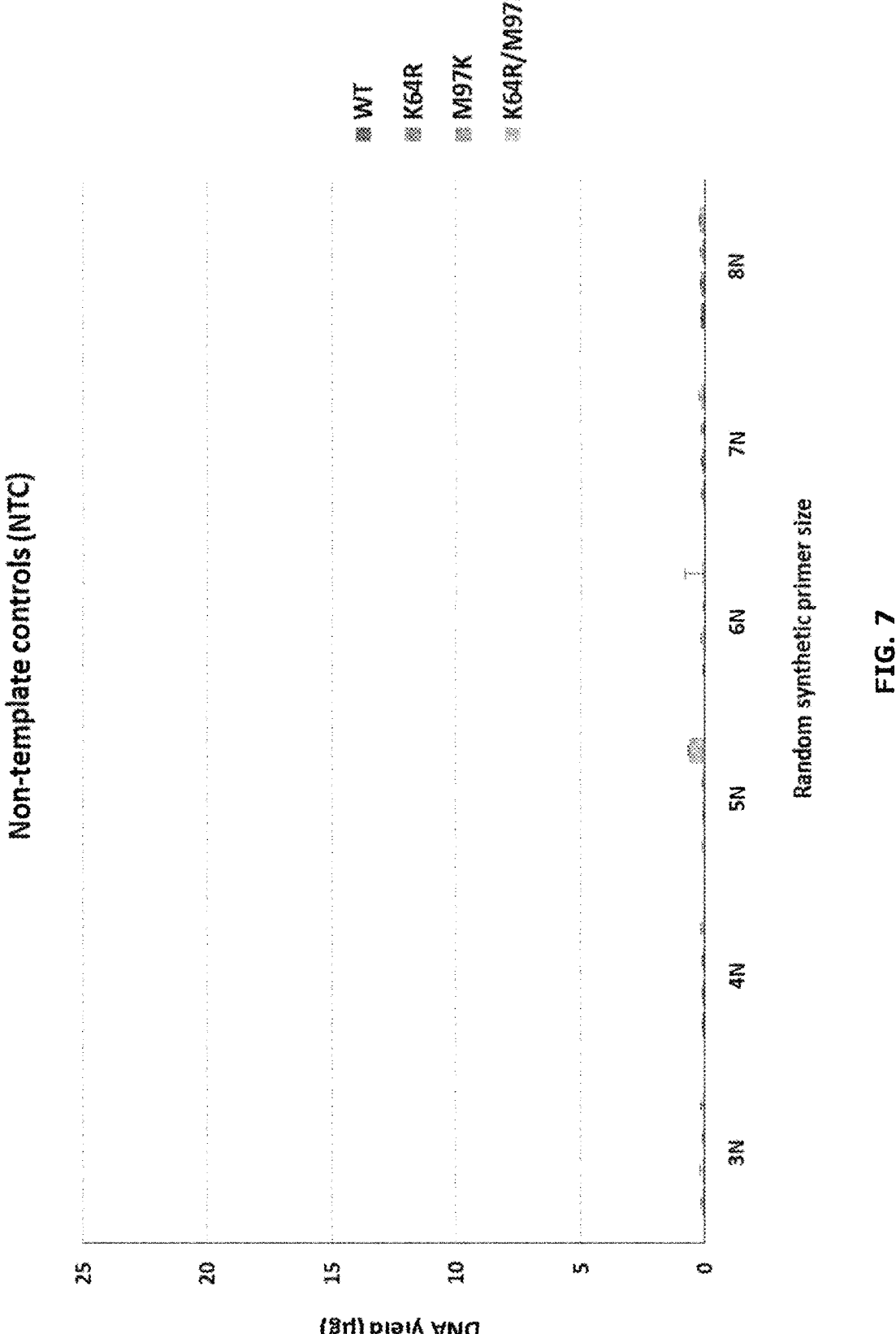
FIG. 7. Amplification yield observed in the absence of input DNA with either WT Phi29 DNApol, mutant K64R, mutant M97K or double mutant K64R/M97K, in combination with random synthetic primers of different sizes: trimers (3N), tetramers (4N), pentamers (5N), hexamers (6N), heptamers (7N) or octamers (8N), under high ionic strength conditions. For each primer length N the columns are shown in the following order from left to right: WT Phi29 DNApol, mutant K64R, mutant M97K double mutant K64R/M97K.

Shown in FIG. 7 are the amplification yields observed in the absence of input DNA but increasing the ionic strength conditions by the addition of ammonium sulfate [(NH$_4$)$_2$SO$_4$]. In the presence of ammonium sulfate (45 mM), amplification levels observed in the absence of input DNA are completely eliminated in all variants and all primer sizes.

Figure 8:
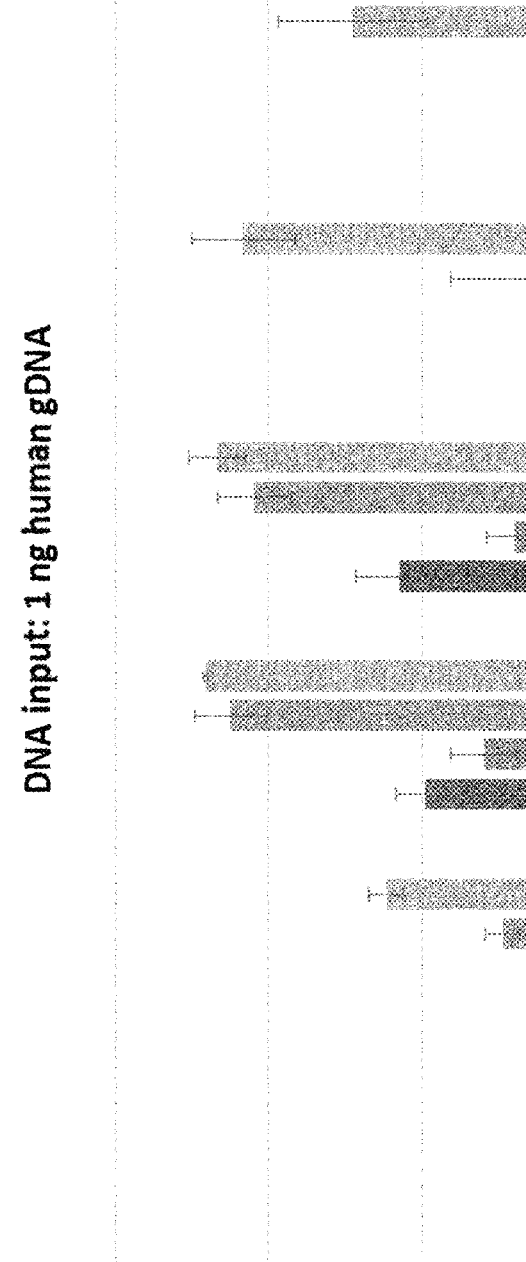
FIG. 8. Amplification efficiency of WT Phi29 DNApol, mutant K64R, mutant M97K and double mutant K64R/M97K, in combination with random primers of different lengths: trimers (3N), tetramers (4N), pentamers (5N), hexamers (6N), heptamers (7N) or octamers (8N), using 1 ng of human genomic DNA as input in the reaction, under high ionic strength conditions. For each primer length N the columns are shown in the following order from left to right: WT Phi29 DNApol, mutant K64R, mutant M97K double mutant K64R/M97K.

Example 5: High Ionic Strength Conditions Reinforce the Robustness and Efficiency of Double Mutant K64R/M97K for the Amplification of DNA Using Random Primers of Different Lengths Shown in FIG. 8 is the amplification of 1 ng of human genomic DNA by multiple displacement amplification (MDA) combining WT Phi29 DNApol or the selected inventive variants (K64R, M97K and K64R/M97K) and random synthetic primers of different sizes: trimers (3N), tetramers (4N), pentamers (5N), hexamers (6N), heptamers (7N) or octamers (8N), under high ionic strength conditions (20 mM KCl; 57 mM NaCl; 45 mM (NH$_4$)$_2$SO$_4$). Amplification yields shown are the mean of two independent experiments that included 3 replicates per condition each. Standard deviation from the two experiments is depicted.

As observed in FIG. 8, none of the enzymes tested were able to efficiently amplify genomic DNA using random synthetic trimers. Only the double mutant K64R/M97K showed a yield close to 600 ng.

As opposed to what was observed in previous conditions (see FIG. 5), tetramers were efficiently used only by M97K single mutant and K64R/M97K double mutant, while single mutant K64R produced only a minor yield close to 1 μg. Remarkably, the amplification yields observed for M97K single mutant and K64R/M97K double mutant increased in comparison to the ones obtained in the absence of ammonium sulfate (from 4 to 12, and from 13 to 16 μg respectively).

In the case of pentamers and hexamers, M97K single mutant and K64R/M97K double mutant showed similar results, clearly overcoming the amplification yields obtained with the WT enzyme or the K64R variant. As it was shown in the absence of ammonium sulfate, WT Phi29 DNApol showed higher yields than K64R variant.

In the case of heptamers, only double mutant K64R/M97K maintained the amplification yield obtained with shorter random synthetic primers and/or in the absence of ammonium sulfate. Both WT Phi29 DNApol and K64R variant significantly decreased the yield, showing the same values in these conditions. The yield obtained with the M97K mutant was also reduced in comparison to previous conditions.

Lastly, octamers were only efficiently deployed by the double mutant K64R/M97K, while the other three enzymes showed very low amplification yields.

Figure 2:
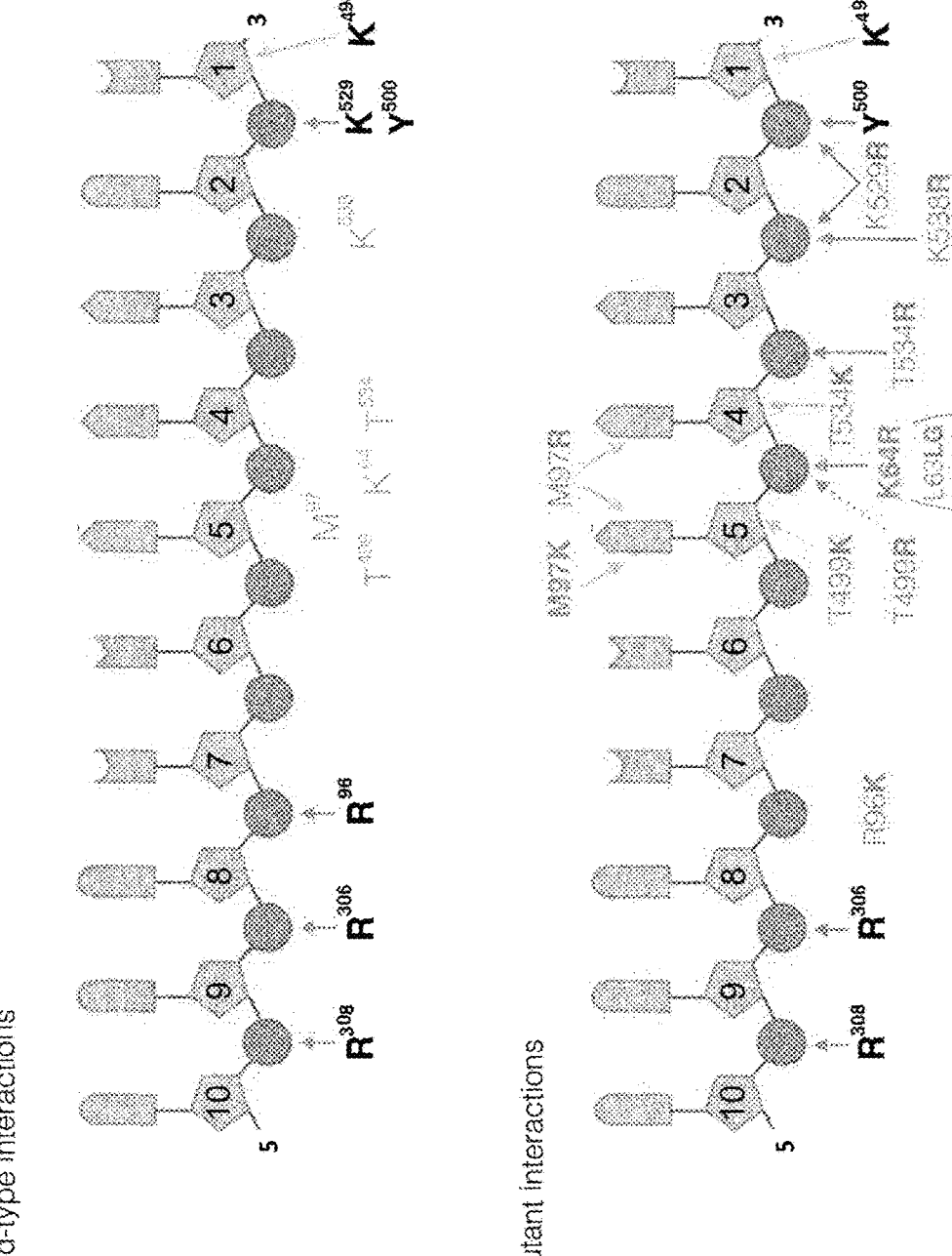
FIG. 2. A) Schematic view of the wild-type (WT) Phi29 DNApol amino acid residues involved in interaction with the first 10 nucleotide of the primer strand, as derived from the crystal structure (PDB id: 2PYL). Nucleotide numbered as 1 is the most 3'-terminal, frequently described as "primer terminus", and the one closest to the enzyme active site. B) The scheme shows the gain of novel interactions with the primer strand, originated by the different mutations indicated (magenta). The colored arrows indicate if the interaction involves the phosphodiester (red), the sugar (orange) or the base (green). Mutants T499K and T499R are predicted to interact with the same positions of the complementary/template strand (indicated with dashed-line arrows).

Phi29 DNApol double mutant K64R/M97K keeps intact the amplification performance under both low and high ionic strength conditions, likely as a consequence of the gain of function acquired by the additional contacts of the enzyme with the nitrogen base from primer nucleotide 5 and the phosphodiester bond between nucleotides 4 and 5 (see FIG. 2). These additional contacts enable the enzyme to proficiently stabilize primers of different sizes under different ionic strength conditions.

Figure 9:
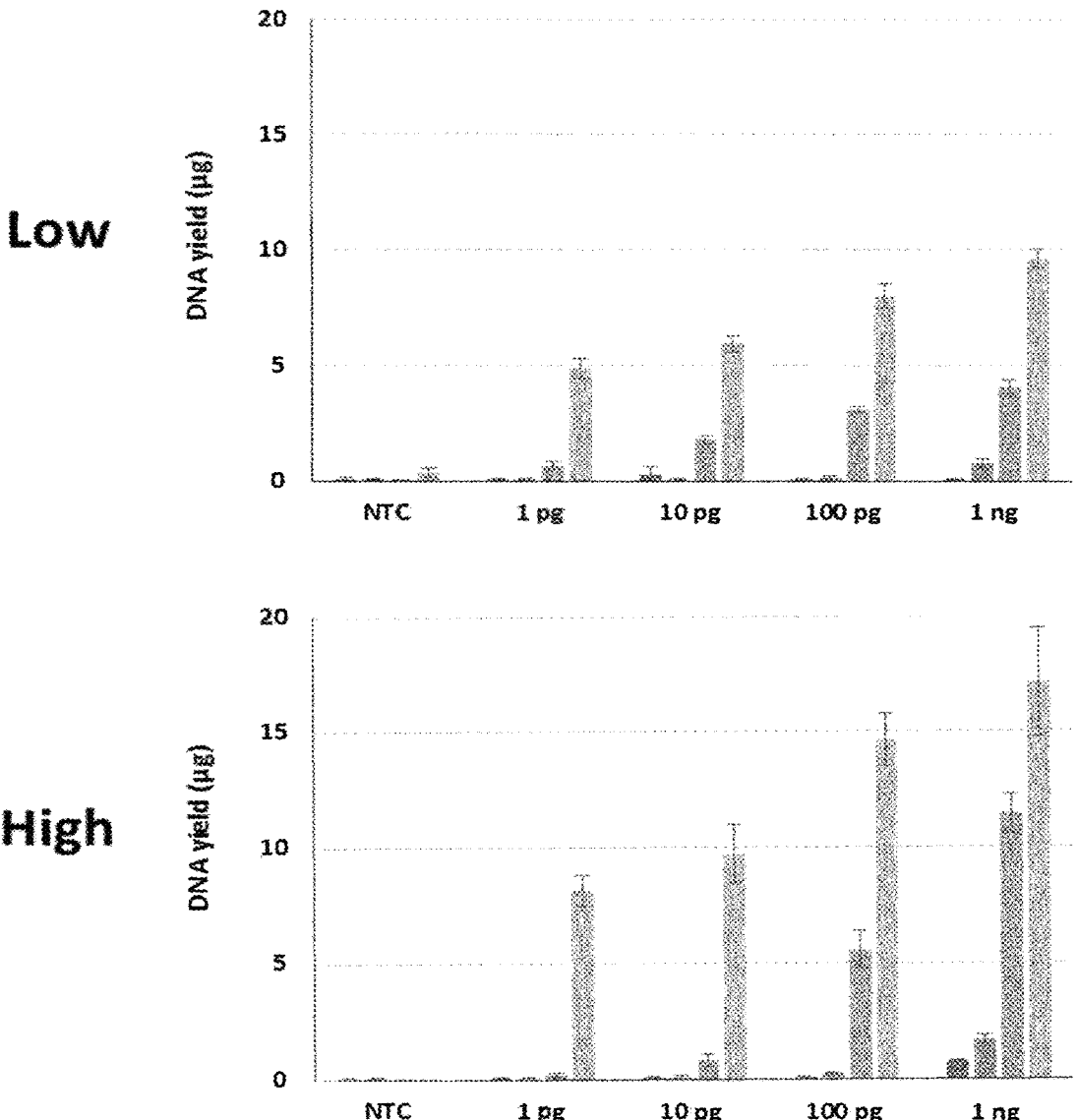
FIG. 9. Amplification efficiency of WT Phi29 DNApol, mutant K64R, mutant M97K and double mutant K64R/M97K, in combination with random primers of different lengths (tetramers (4N), pentamers (5N), hexamers (6N)), using different human genomic DNA inputs (1, 10, 100 pg and 1 ng) in the reaction, under low and high ionic strength conditions. For each primer length N the columns are shown in the following order from left to right: WT Phi29 DNApol, mutant K64R, mutant M97K double mutant K64R/M97K.
Figure 9:
Figure 9:
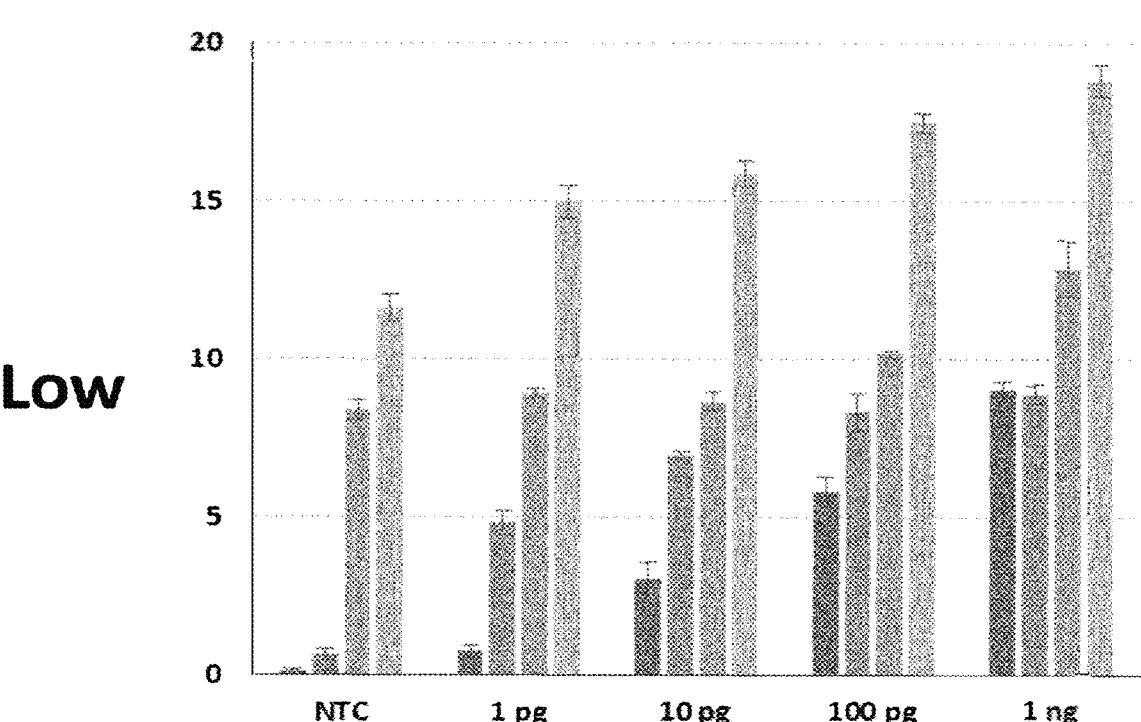
Figure 9:
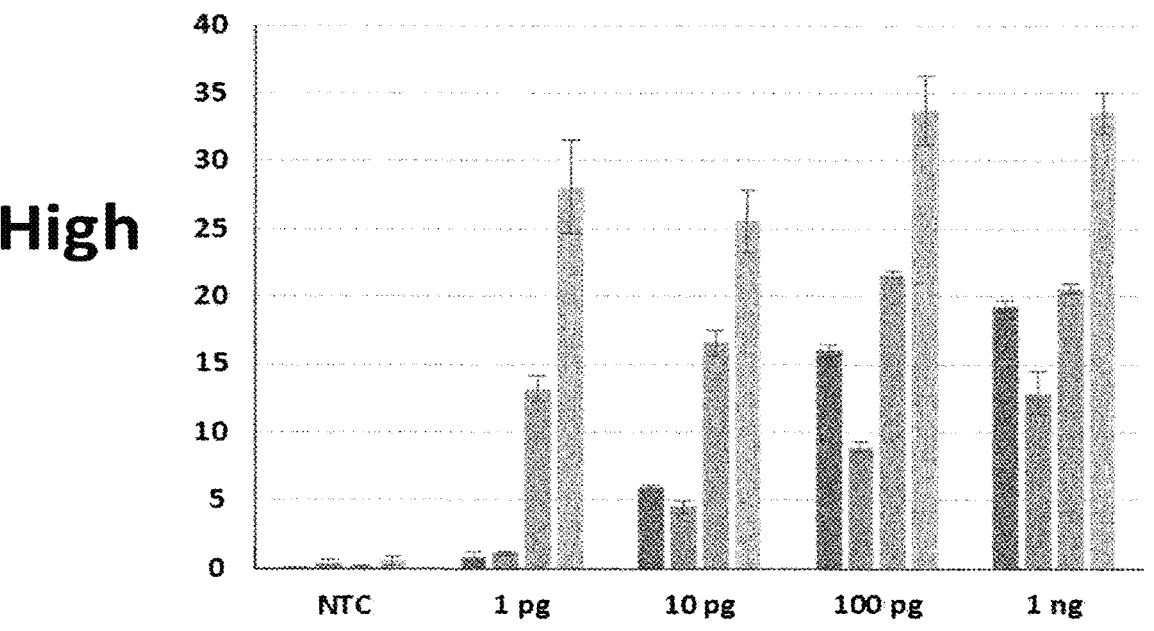
Figure 9:
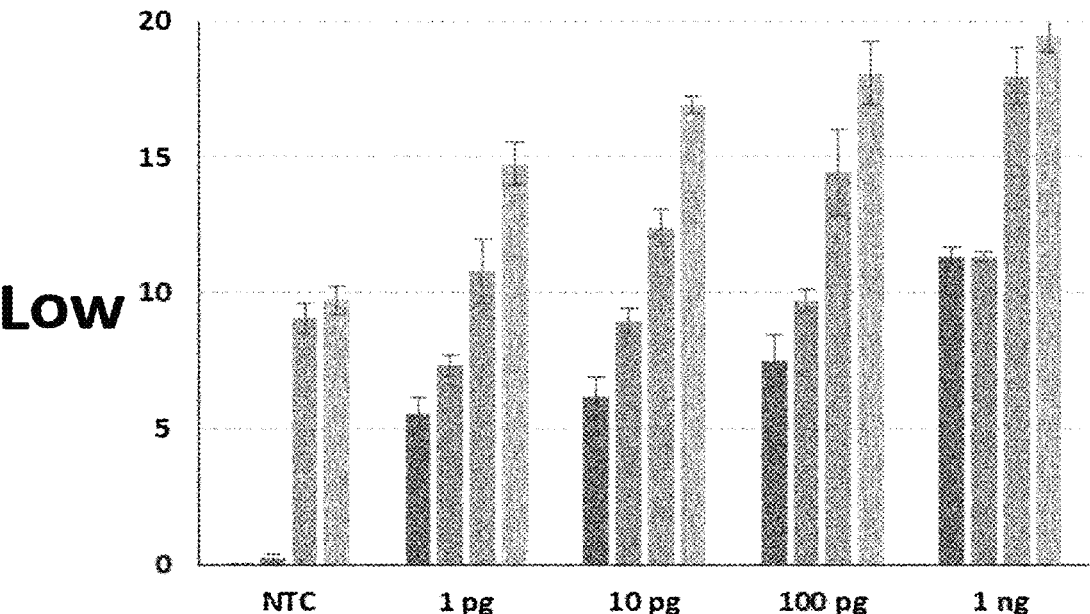
Figure 9:
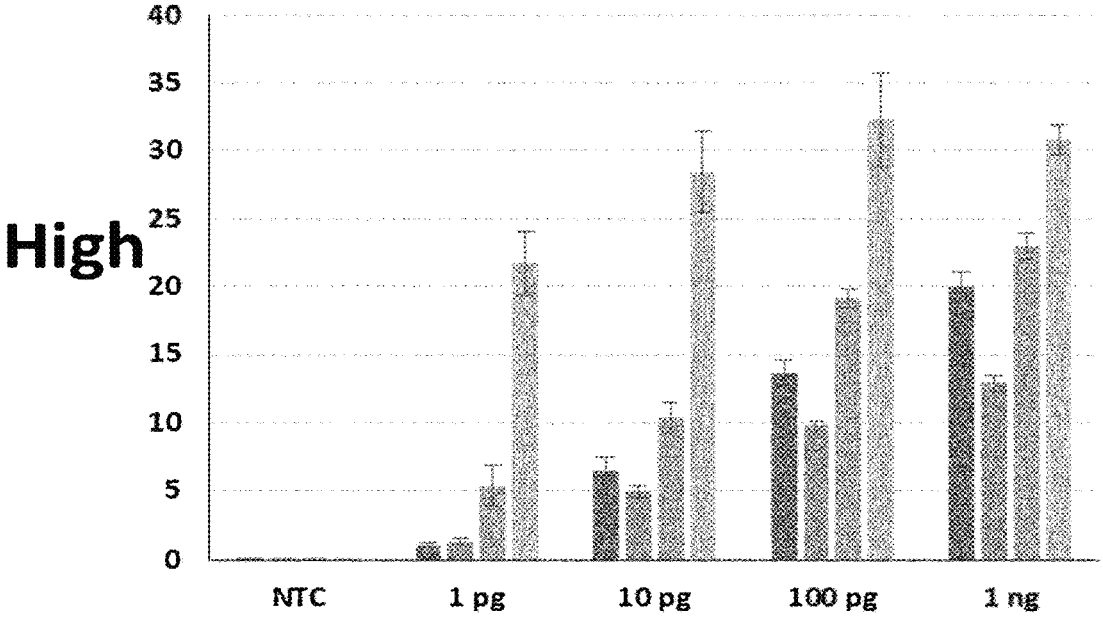

Example 6: Double Mutation K64R/M97K Results in a Very Sensitive Amplification of Minute Amounts of DNA Independently of the Primer Size Tested Shown in FIG. 9 is the amplification of different amounts of human genomic DNA (1, 10, 100 pg and 1 ng) by multiple displacement amplification (MDA) combining WT Phi29

DNApol or the selected inventive variants (K64R, M97K and K64R/M97K) and random synthetic primers of different sizes: tetramers (4N), pentamers (5N) or hexamers (6N), under low (20 mM KCl; 57 mM NaCl) or high (20 mM KCl; 57 mM NaCl; 45 mM $(NH_4)_2SO_4$) ionic strength conditions.

Under low ionic strength conditions (FIG. 9, higher panels), double mutant K64R/M97K produces the most consistent and the highest amplification yields in all conditions tested.

In the case of random synthetic tetramers, as it was previously shown (see FIG. 5), WT Phi29 DNApol was not able to amplify any of the DNA inputs tested. Variant K64R produced a detectable yield only with 1 ng of DNA input, lacking sensitivity to amplify lower DNA amounts. On the contrary, both M97K and M97K/K64R mutants efficiently amplified the DNA inputs tested, the double mutant producing higher yields in all cases.

In the case of random synthetic pentamers, all enzymes were able to use them to start off the amplification, but showing different levels of sensitivity and efficiency. WT Phi29 DNApol showed a significant decrease in the amplification yield when the amount of DNA input descended, while the three inventive variants maintained a reasonable efficiency in all conditions tested. Double mutant M97K/K64R displayed the highest amplification efficiency among the three inventive variants independently of the DNA input amount, therefore showing the best sensitivity.

In the case of random synthetic hexamers, all enzymes were able to use them efficiently to initiate the amplification of each DNA input tested, showing notable amplification yields in every case. The three inventive variants overcame WT Phi29 DNApol, showing higher amplification yields when low DNA inputs were analyzed. As it occurred with pentamers, double mutant M97K/K64R displayed the highest amplification efficiency among the three inventive variants independently of the DNA input amount.

As it was previously shown (see FIG. 6), both M97K and M97K/K64R variants showed significant amplification yields in the absence of input DNA (non-template controls, NTC) when using pentamers and hexamers. For this reason, the same sensitivity analysis was carried out under high ionic strength conditions (20 mM KCl; 57 mM NaCl; 45 mM $(NH_4)_2SO_4$) to prevent this artifactual effect derived from primer-dimer amplification.

Under high ionic strength conditions (see FIG. 9, lower panels), random synthetic tetramers showed a similar pattern of usage among the variants tested in comparison to low ionic strength conditions, although the amplification yields were increased in most cases. The exception to this rule was the variant M97K that showed lower yields with 1 pg and 10 pg DNA inputs.

In the case of random synthetic pentamers under high ionic strength conditions, M97K and M97K/K64R variants showed the best performance in terms of sensitivity and efficiency, showing higher amplification yields in comparison to low ionic strength conditions with the same DNA input amounts. The increase in the ionic strength of the reaction produced a reduction in the amplification efficiency of variant K64R when limiting amounts of DNA were tested (1 and 10 pg), while the efficiency was similar (100 pg) or higher (1 ng) with the other two inputs. Surprisingly, WT Phi29 DNApol overcame K64R variant under these conditions in all cases.

In the case of random synthetic hexamers under high ionic strength conditions, double mutant K64R/M97K was the only variant that increased the yields observed with all DNA inputs in comparison to the results obtained under low ionic strength conditions. Single mutant M97K showed lower yields with the lowest inputs (1 and 10 pg), while increasing the yields with 100 pg and 1 ng DNA inputs, indicating a decrease in sensitivity. Variant K64R and WT Phi29 DNApol showed a similar behavior. As it occurred with pentamers, WT Phi29 DNApol produced higher amplification yields than K64R variant under these conditions in all cases.

In summary, double mutant K64R/M97K showed the best performance in terms of amplification efficiency and sensitivity under both low and high ionic strength conditions during the amplification reaction with all DNA primers tested.

Example 7: Amplification Efficiency and Sensitivity are not Modified by the Use of the Inventive Variants when Primers are Generated by TthPrimPol Shown in FIG. 10 is the amplification of 1, 10, 100 pg and 1 ng of human genomic DNA by multiple displacement amplification (MDA) combining WT Phi29 DNApol or the selected inventive variants (K64R, M97K and K64R/M97K) and TthPrimPol, a DNA primase capable of synthesizing primers in the course of the reaction for Phi29 DNApol (Picher et al, 2016).

Figure 10:
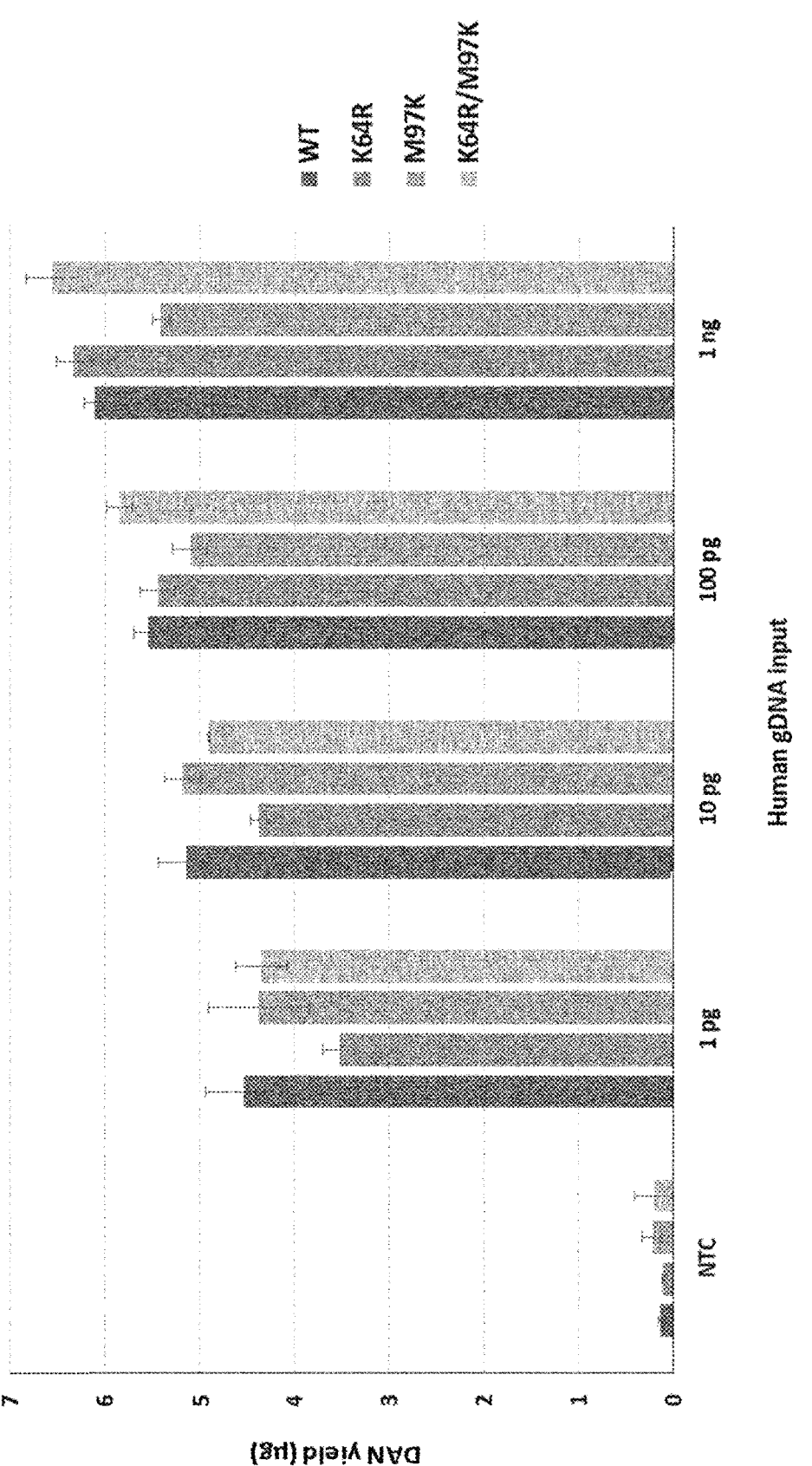
FIG. 10. Amplification of 1, 10, 100 pg and 1 ng of human genomic DNA by multiple displacement amplification (MDA) combining Phi29 DNApol variants and TthPrimPol. For each amount of DNA the columns are shown in the following order from left to right: WT Phi29 DNApol, mutant K64R, mutant M97K double mutant K64R/M97K.

As observed in FIG. 10, there are no significant yield differences between the WT Phi29 DNA pol and the inventive variants tested, which results in similar sensitivity and efficiency levels under this setup.

Example 8: Selected Inventive Variants (K64R, M97K and K64R/M97K) Improve the Amplification Coverage Measured by CovCheck Technology CovCheck technology allows the coverage analysis of whole genome amplifications using a PCR panel including 24 different primer pairs that amplify small portions from each human chromosome. CovCheck technology has been validated by comparing CovCheck coverage values with real coverage obtained through low-pass whole genome sequencing, obtaining excellent correlation values (https://www.expedeon.com/products/genomics/dna-rna-products/covcheck-per-kits/).

In order to analyze the amplification coverage obtained with each variant, a limited amount of input material was selected: 30 pg of human genomic DNA. This DNA amount is equivalent to 5 human diploid genomes, and it might be the lowest amount ensuring that sufficient copies of each chromosome will be available for the amplification. Below this level, certain regions or complete chromosomes could be absent in the input for the amplification due to the random distribution of molecules in a purified DNA sample, resulting in regions not covered in the amplified material due to the absence of the template, and not due to amplification failures.

Figure 11:
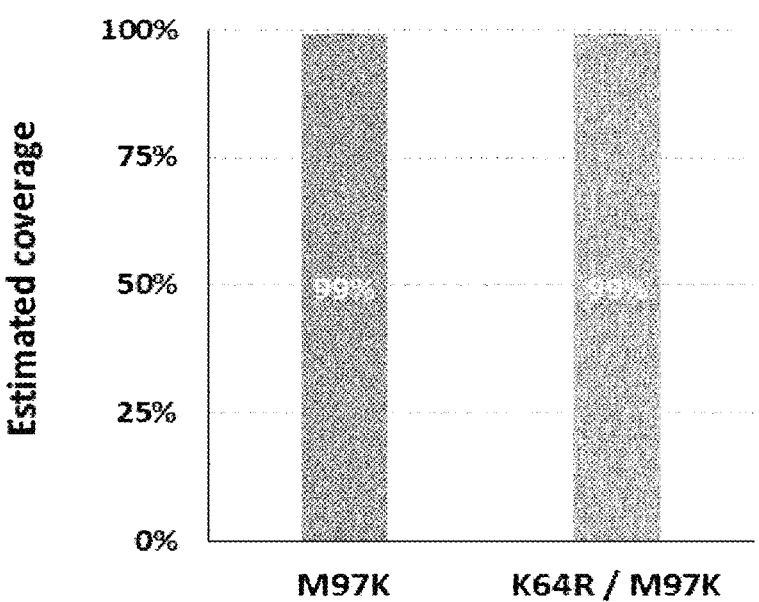
FIG. 11. Estimated coverage values obtained from the CovCheck analysis of amplification reactions using hexamers (6N), pentamers (5N) and tetramers (4N), in combination with Phi29 DNApol variants and different human genomic DNA inputs in each case to reach conditions in which coverage differences can be observed.
Figure 11:
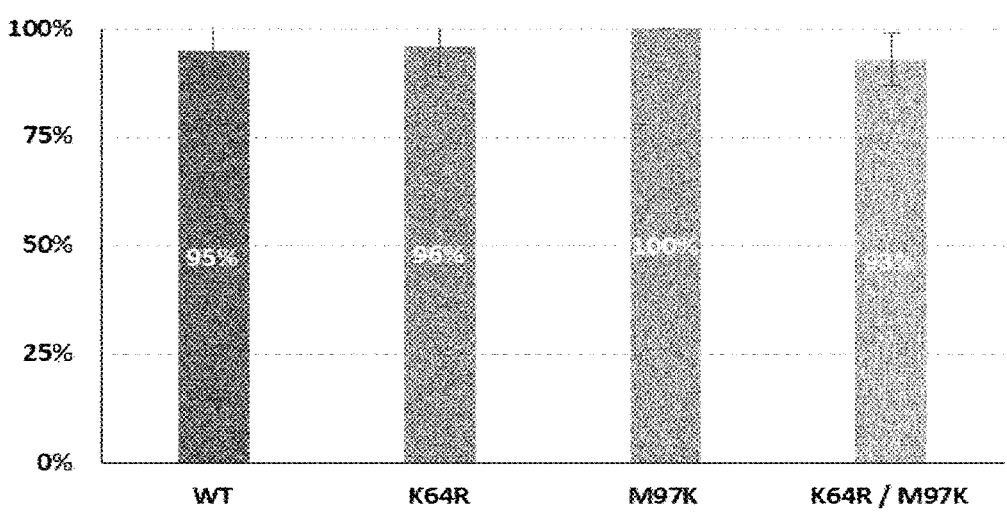
Figure 11:
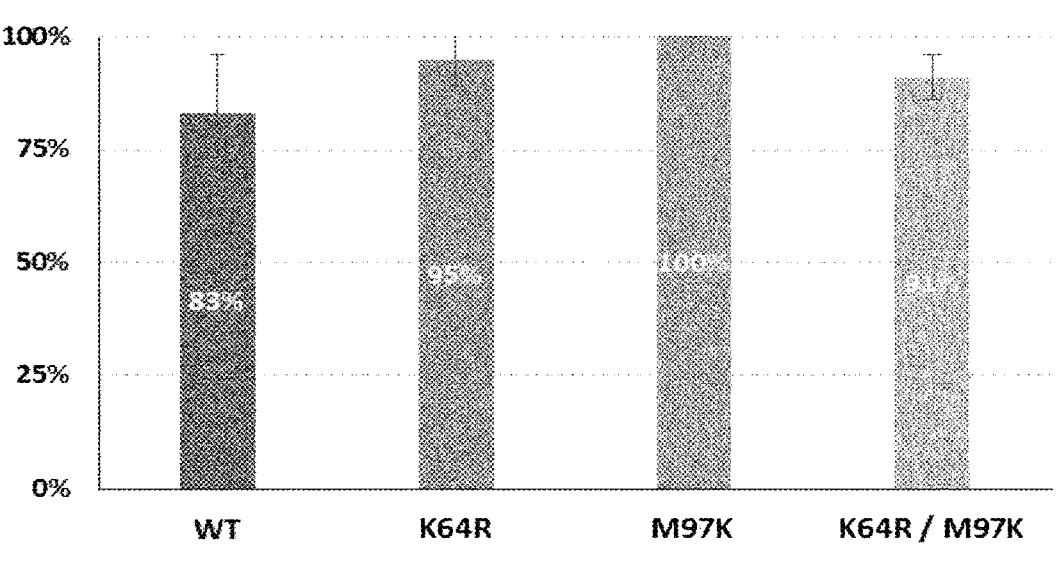

Shown in FIG. 11 is the estimated coverage values obtained from the CovCheck analysis of amplification reactions using hexamers, pentamers and tetramers, in combination with WT Phi29 DNApol or the selected inventive variants and 30 pg of human genomic DNA input. Coverage values are means of 6 independent reactions per condition.

In the case of random synthetic hexamers, amplification coverage is improved when using the three inventive variants in comparison to the value obtained by the WT Phi29 DNApol.

In the case of random synthetic pentamers, all enzymes showed coverage values above 90% in these conditions. Therefore, no significant differences could be observed. However, M97K variant stood out with a perfect coverage in the 6 replicates tested.

In the case of random synthetic tetramers, only M97K and M97K/K64R variants produced amplified DNA, which is consistent with the sensitivity of amplification shown by WT Phi29 DNApol and K64R variant when combined with tetramers (FIG. 9). The CovCheck analysis revealed an excellent amplification coverage in both cases (99%), pointing to the benefit of using the inventive variants in combination with the shortest primers possible, in order to maximize the amplification coverage and uniformity, preventing amplification biases and loss of sequences.

Figure 12:
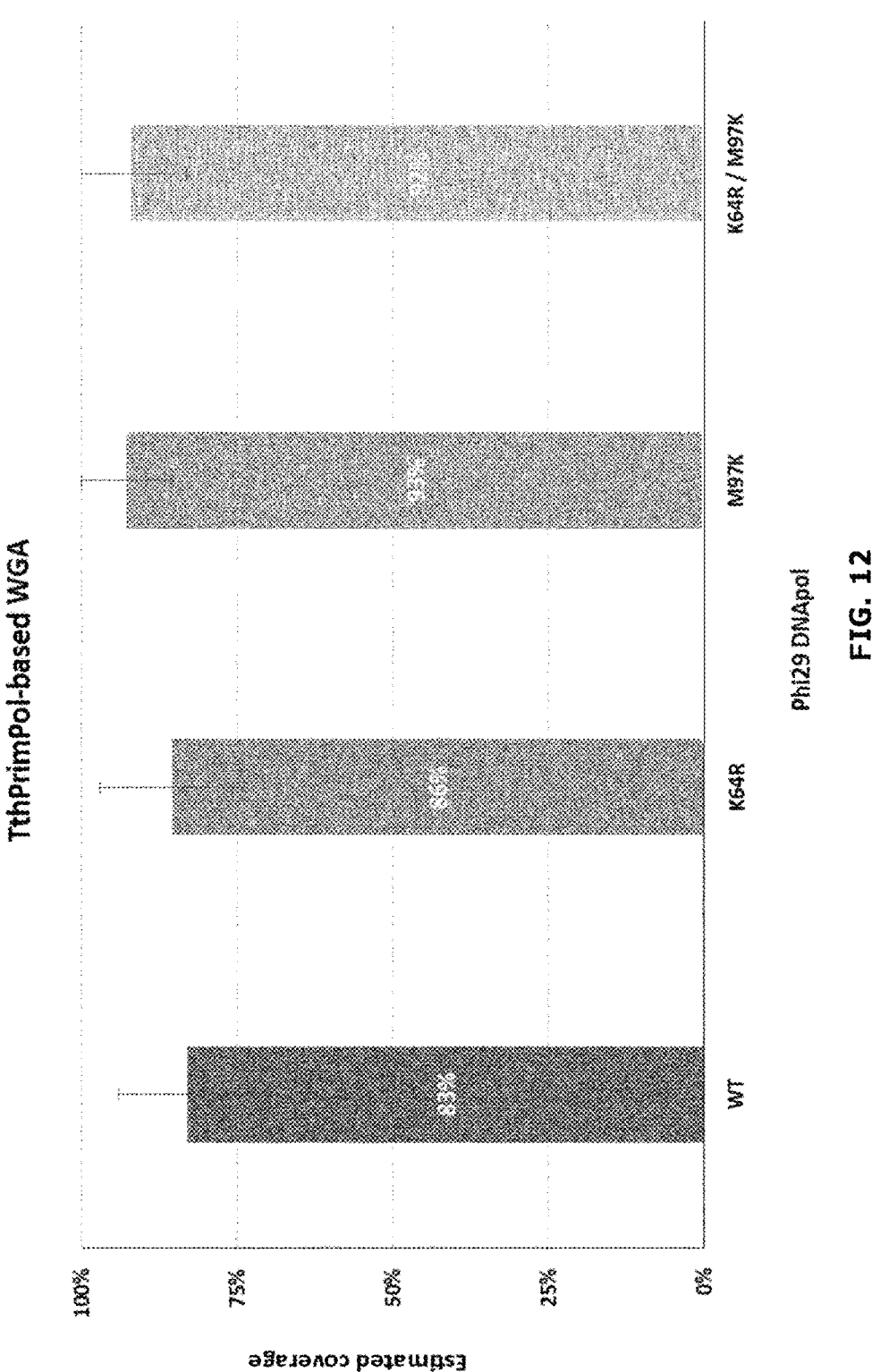
FIG. 12. Estimated coverage values obtained from the CovCheck analysis of amplification reactions carried out by TthPrimPol in combination with Phi29 DNApol variants.

In the case of using an enzyme (TthPrimPol) make DNA primers for Phi29 DNApol, FIG. 12 shows the estimated coverage values obtained from the CovCheck analysis of amplification reactions carried out by the combination of TthPrimPol with WT Phi29 DNApol or the inventive variants, using 30 pg (5 genome equivalents) of human genomic DNA as input in the amplification reaction. Coverage values are means of 12 independent reactions per condition. The CovCheck analysis also revealed an improvement in amplification coverage when using the inventive variants, supporting the advantage of those to enhance the uniformity of the amplified material with respect to the original DNA input.

REFERENCES (INCORPORATED HEREIN BY REFERENCE)

Blanco L, Salas M. Characterization and purification of a phage phi 29-encoded DNA polymerase required for the initiation of replication. *Proc Natl Acad Sci USA.* 1984 September; 81(17):5325-9.

Blanco L, Salas M. Characterization of a 3'-5' exonuclease activity in the phage phi 29-encoded DNA polymerase. *Nucleic Acids Res.* 1985 Feb. 25; 13(4):1239-49.

Bernad A, Zaballos A, Salas M, Blanco L. Structural and functional relationships between prokaryotic and eukaryotic DNA polymerases. *EMBO J.* 1987 Dec. 20; 6(13): 4219-25.

Rodriguez I, Lázaro J M, Blanco L, Kamtekar S, Berman A J, Wang J, Steitz T A, Salas M, de Vega M. A specific subdomain in ø29 DNA polymerase confers both processivity and strand-displacement capacity *Proc. Natl. Acad. Sci. USA* 2005 May 3; 102(18):6407-12.

Kamtekar, S. Berman, A J, Wang, J, Lázaro, J M, de Vega, M, Blanco L, Salas M and Steitz T A. The phi29 DNA polymerase:protein-primer structure suggests a model for the initiation to elongation transition *EMBO J.* 2006 Mar. 22; 25(6):1335-43. Epub 2006 Mar. 2.

Berman A J, Kamtekar S, Goodman J L, Lázaro J M, de Vega M, Blanco L, Salas M, and Steitz T A. Structures of phi29 DNA polymerase complexed with substrate: the mechanism of translocation in B-family polymerases. *EMBO J.* 2007 Jul. 25; 26(14):3494-505.

Blanco L, Bernad A, Lázaro J M, Martin G, Garmendia C, Salas M. Highly efficient DNA synthesis by the phage phi 29 DNA polymerase. Symmetrical mode of DNA replication. *J Biol Chem.* 1989 May 25; 264(15):8935-40.

Esteban J A, Salas M, Blanco L. Fidelity of phi 29 DNA polymerase. Comparison between protein-primed initiation and DNA polymerization. *J Biol Chem.* 1993 Feb. 5; 268(4):2719-26.

Esteban J A, Soengas M S, Salas M, Blanco L. 3'→5' exonuclease active site of phi 29 DNA polymerase. Evidence favoring a metal ion-assisted reaction mechanism. *J Biol Chem.* 1994 Dec. 16; 269(50):31946-54.

Dean F B, Hosono S, Fang L, Wu X, Faruqi A F, Bray-Ward P, Sun Z, Zong Q, Du Y, Du J, Driscoll M, Song W, Kingsmore S F, Egholm M, Lasken R S. Comprehensive human genome amplification using multiple displacement amplification. *Proc Natl Acad Sci USA.* 2002 Apr. 16; 99(8):5261-6.

Lizardi P M, Huang X, Zhu Z, Bray-Ward P, Thomas D C, Ward D C. Mutation detection and single-molecule counting using isothermal rolling-circle amplification. *Nat Genet.* 1998 July; 19(3):225-32.

Picher A J, Budeus B, Wafzig O, Kruger C, Garcia-Gómez S, Martinez-Jiménez MI, Díaz-Talavera A, Weber D, Blanco L & Schneider A. TruePrime is a novel method for whole-genome amplification from single cells based on TthPrimPol. *Nat Comm* 2016, Nov. 29; 7:13296.

Alsmadi O, Alkayal F, Monies D, Meyer B F. Specific and complete human genome amplification with improved yield achieved by phi29 DNA polymerase and a novel primer at elevated temperature. *BMC Res Notes.* 2009 Mar. 24; 2:48. doi: 10.1186/1756-0500-2-48.

Povilaitis T, Alzbutas G, Sukackaite R, Siurkus J, Skirgaila R. In vitro evolution of phi29 DNA polymerase using isothermal compartmentalized self-replication technique. *Protein Eng Des Sel.* 2016 December; 29(12):617-628. Epub 2016 Sep. 26.

U.S. Pat. No. 5,656,493A, "System for automated performance of the polymerase chain reaction", Feb. 18, 1994.

Maxam A M, Gilbert W. A new method for sequencing DNA. *Proc Natl Acad Sci USA.* 1977 February; 74(2): 560-4.

Sanger F, Nicklen S, Coulson A R. DNA sequencing with chain-terminating inhibitors. *Proc Natl Acad Sci USA.* 1977 December; 74(12):5463-7.

Sanger F, Coulson A R. The use of thin acrylamide gels for DNA sequencing. *FEBS Lett.* 1978 Mar. 1; 87(1):107-10.

Metzker M L. Sequencing technologies—the next generation. *Nat Rev Genet.* 2010 January; 11(1):31-46.

Sam L T, Lipson D, Raz T, Cao X, Thompson J, Milos P M, Robinson D, Chinnaiyan A M, Kumar-Sinha C, Maher C A. A comparison of single molecule and amplification based sequencing of cancer transcriptomes. *PLoS One.* 2011 Mar. 1; 6(3):e17305.

Thompson J F, Milos P M. The properties and applications of single-molecule DNA sequencing. *Genome Biol.* 2011; 12(2):217.

WO 2011/047307A1, "Multiple Displacement Amplification", Apr. 21, 2011.

Garmendia C, Bernad A, Esteban J A, Blanco L, Salas M. The bacteriophage phi 29 DNA polymerase, a proofreading enzyme. *J Biol Chem.* 1992 Feb. 5; 267(4):2594-9.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". In certain embodiments, inventions that "comprise" varies elements also may "consisting essentially of" these elements. The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

All publications, patents, and patent applications mentioned in this specification are herein incorporated by reference to the same extent as if each individual publication, patent, or patent application was specifically and individually indicated to be incorporated by reference.

```
SEQUENCE LISTING
Amino acids in italics are not expressed in some embodiments
SEQ ID NO 1: Wild-type Phi29 DNA polymerase (UniProtKB-
P03680)
Met Lys His Met Pro Arg Lys Met Tyr Ser Cys Asp Phe Glu Thr
1            5                10                15

Thr Thr Lys Val Glu Asp Cys Arg Val Trp Ala Tyr Gly Tyr Met
             20              25                30

Asn Ile Glu Asp His Ser Glu Tyr Lys Ile Gly Asn Ser Leu Asp
             35              40                45

Glu Phe Met Ala Trp Val Leu Lys Val Gln Ala Asp Leu Tyr Phe
             50              55                60

His Asn Leu Lys Phe Asp Gly Ala Phe Ile Ile Asn Trp Leu Glu
             65              70                75

Arg Asn Gly Phe Lys Trp Ser Ala Asp Gly Leu Pro Asn Thr Tyr
             80              85                90

Asn Thr Ile Ile Ser Arg Met Gly Gln Trp Tyr Met Ile Asp Ile
             95              10               105

Cys Leu Gly Tyr Lys Gly Lys Arg Lys Ile His Thr Val Ile Tyr
             110             115               120

Asp Ser Leu Lys Lys Leu Pro Phe Pro Val Lys Lys Ile Ala Lys
             125             130               135

Asp Phe Lys Leu Thr Val Leu Lys Gly Asp Ile Asp Tyr His Lys
             140             145               150

Glu Arg Pro Val Gly Tyr Lys Ile Thr Pro Glu Glu Tyr Ala Tyr
             155             160               165

Ile Lys Asn Asp Ile Gln Ile Ile Ala Glu Ala Leu Leu Ile Gln
             170             175               180

Phe Lys Gln Gly Leu Asp Arg Met Thr Ala Gly Ser Asp Ser Leu
             185             190               195

Lys Gly Phe Lys Asp Ile Ile Thr Thr Lys Lys Phe Lys Lys Val
             200             205               210

Phe Pro Thr Leu Ser Leu Gly Leu Asp Lys Glu Val Arg Tyr Ala
             215             220               225

Tyr Arg Gly Gly Phe Thr Trp Leu Asn Asp Arg Phe Lys Glu Lys
             230             235               240

Glu Ile Gly Glu Gly Met Val Phe Asp Val Asn Ser Leu Tyr Pro
             245             250               255

Ala Gln Met Tyr Ser Arg Leu Leu Pro Tyr Gly Glu Pro Ile Val
             260             265               270
```

-continued

```
Phe Glu Gly Lys Tyr Val Trp Asp Glu Asp Tyr Pro Leu His Ile
            275             280             285

Gln His Ile Arg Cys Glu Phe Glu Leu Lys Glu Gly Tyr Ile Pro
            290             295             300

Thr Ile Gln Ile Lys Arg Ser Arg Phe Tyr Lys Gly Asn Glu Tyr
            305             310             315

Leu Lys Ser Ser Gly Gly Glu Ile Ala Asp Leu Trp Leu Ser Asn
            320             325             330

Val Asp Leu Glu Leu Met Lys Glu His Tyr Asp Leu Tyr Asn Val
            335             340             345

Glu Tyr Ile Ser Gly Leu Lys Phe Lys Ala Thr Thr Gly Leu Phe
            350             355             360

Lys Asp Phe Ile Asp Lys Trp Thr Tyr Ile Lys Thr Thr Ser Glu
            365             370             375

Gly Ala Ile Lys Gln Leu Ala Lys Leu Met Leu Asn Ser Leu Tyr
            380             385             390

Gly Lys Phe Ala Ser Asn Pro Asp Val Thr Gly Lys Val Pro Tyr
            395             400             405

Leu Lys Glu Asn Gly Ala Leu Gly Phe Arg Leu Gly Glu Glu Glu
            410             415             420

Thr Lys Asp Pro Val Tyr Thr Pro Met Gly Val Phe Ile Thr Ala
            425             430             435

Trp Ala Arg Tyr Thr Thr Ile Thr Ala Ala Gln Ala Cys Tyr Asp
            440             445             450

Arg Ile Ile Tyr Cys Asp Thr Asp Ser Ile His Leu Thr Gly Thr
            455             460             465

Glu Ile Pro Asp Val Ile Lys Asp Ile Val Asp Pro Lys Lys Leu
            470             475             480

Gly Tyr Trp Ala His Glu Ser Thr Phe Lys Arg Ala Lys Tyr Leu
            485             490             495

Arg Gln Lys Thr Tyr Ile Gln Asp Ile Tyr Met Lys Glu Val Asp
            500             505             510

Gly Lys Leu Val Glu Gly Ser Pro Asp Asp Tyr Thr Asp Ile Lys
            515             520             525

Phe Ser Val Lys Cys Ala Gly Met Thr Asp Lys Ile Lys Lys Glu
            530             535             540

Val Thr Phe Glu Asn Phe Lys Val Gly Phe Ser Arg Lys Met Lys
            545             550             555

Pro Lys Pro Val Gln Val Pro Gly Gly Val Val Leu Val Asp Asp
            560             565             570

Thr Phe Thr Ile Lys
            575
```

SEQ ID NO 2: K64R Phi29DNApol mutant

```
Met Lys His Met Pro Arg Lys Met Tyr Ser Cys Asp Phe Glu Thr
1           5               10              15

Thr Thr Lys Val Glu Asp Cys Arg Val Trp Ala Tyr Gly Tyr Met
            20              25              30

Asn Ile Glu Asp His Ser Glu Tyr Lys Ile Gly Asn Ser Leu Asp
            35              40              45

Glu Phe Met Ala Trp Val Leu Lys Val Gln Ala Asp Leu Tyr Phe
            50              55              60

His Asn Leu Arg Phe Asp Gly Ala Phe Ile Ile Asn Trp Leu Glu
            65              70              75
```

-continued

```
Arg Asn Gly Phe Lys Trp Ser Ala Asp Gly Leu Pro Asn Thr Tyr
             80                  85                  90

Asn Thr Ile Ile Ser Arg Met Gly Gln Trp Tyr Met Ile Asp Ile
             95                 100                 105

Cys Leu Gly Tyr Lys Gly Lys Arg Lys Ile His Thr Val Ile Tyr
            110                 115                 120

Asp Ser Leu Lys Lys Leu Pro Phe Pro Val Lys Lys Ile Ala Lys
            125                 130                 135

Asp Phe Lys Leu Thr Val Leu Lys Gly Asp Ile Asp Tyr His Lys
            140                 145                 150

Glu Arg Pro Val Gly Tyr Lys Ile Thr Pro Glu Glu Tyr Ala Tyr
            155                 160                 165

Ile Lys Asn Asp Ile Gln Ile Ile Ala Glu Ala Leu Leu Ile Gln
            170                 175                 180

Phe Lys Gln Gly Leu Asp Arg Met Thr Ala Gly Ser Asp Ser Leu
            185                 190                 195

Lys Gly Phe Lys Asp Ile Ile Thr Thr Lys Lys Phe Lys Lys Val
            200                 205                 210

Phe Pro Thr Leu Ser Leu Gly Leu Asp Lys Glu Val Arg Tyr Ala
            215                 220                 225

Tyr Arg Gly Gly Phe Thr Trp Leu Asn Asp Arg Phe Lys Glu Lys
            230                 235                 240

Glu Ile Gly Glu Gly Met Val Phe Asp Val Asn Ser Leu Tyr Pro
            245                 250                 255

Ala Gln Met Tyr Ser Arg Leu Leu Pro Tyr Gly Glu Pro Ile Val
            260                 265                 270

Phe Glu Gly Lys Tyr Val Trp Asp Glu Asp Tyr Pro Leu His Ile
            275                 280                 285

Gln His Ile Arg Cys Glu Phe Glu Leu Lys Glu Gly Tyr Ile Pro
            290                 295                 300

Thr Ile Gln Ile Lys Arg Ser Arg Phe Tyr Lys Gly Asn Glu Tyr
            305                 310                 315

Leu Lys Ser Ser Gly Gly Glu Ile Ala Asp Leu Trp Leu Ser Asn
            320                 325                 330

Val Asp Leu Glu Leu Met Lys Glu His Tyr Asp Leu Tyr Asn Val
            335                 340                 345

Glu Tyr Ile Ser Gly Leu Lys Phe Lys Ala Thr Thr Gly Leu Phe
            350                 355                 360

Lys Asp Phe Ile Asp Lys Trp Thr Tyr Ile Lys Thr Thr Ser Glu
            365                 370                 375

Gly Ala Ile Lys Gln Leu Ala Lys Leu Met Leu Asn Ser Leu Tyr
            380                 385                 390

Gly Lys Phe Ala Ser Asn Pro Asp Val Thr Gly Lys Val Pro Tyr
            395                 400                 405

Leu Lys Glu Asn Gly Ala Leu Gly Phe Arg Leu Gly Glu Glu Glu
            410                 415                 420

Thr Lys Asp Pro Val Tyr Thr Pro Met Gly Val Phe Ile Thr Ala
            425                 430                 435

Trp Ala Arg Tyr Thr Thr Ile Thr Ala Ala Gln Ala Cys Tyr Asp
            440                 445                 450

Arg Ile Ile Tyr Cys Asp Thr Asp Ser Ile His Leu Thr Gly Thr
            455                 460                 465

Glu Ile Pro Asp Val Ile Lys Asp Ile Val Asp Pro Lys Lys Leu
            470                 475                 480
```

-continued

```
Gly Tyr Trp Ala His Glu Ser Thr Phe Lys Arg Ala Lys Tyr Leu
            485             490             495

Arg Gln Lys Thr Tyr Ile Gln Asp Ile Tyr Met Lys Glu Val Asp
            500             505             510

Gly Lys Leu Val Glu Gly Ser Pro Asp Asp Tyr Thr Asp Ile Lys
            515             520             525

Phe Ser Val Lys Cys Ala Gly Met Thr Asp Lys Ile Lys Lys Glu
            530             535             540

Val Thr Phe Glu Asn Phe Lys Val Gly Phe Ser Arg Lys Met Lys
            545             550             555

Pro Lys Pro Val Gln Val Pro Gly Gly Val Val Leu Val Asp Asp
            560             565             570

Thr Phe Thr Ile Lys
            575

SEQ ID NO 3: M97K Phi29DNApol mutant
Met Lys His Met Pro Arg Lys Met Tyr Ser Cys Asp Phe Glu Thr
1           5               10              15

Thr Thr Lys Val Glu Asp Cys Arg Val Trp Ala Tyr Gly Tyr Met
            20              25              30

Asn Ile Glu Asp His Ser Glu Tyr Lys Ile Gly Asn Ser Leu Asp
            35              40              45

Glu Phe Met Ala Trp Val Leu Lys Val Gln Ala Asp Leu Tyr Phe
            50              55              60

His Asn Leu Lys Phe Asp Gly Ala Phe Ile Ile Asn Trp Leu Glu
            65              70              75

Arg Asn Gly Phe Lys Trp Ser Ala Asp Gly Leu Pro Asn Thr Tyr
            80              85              90

Asn Thr Ile Ile Ser Arg Lys Gly Gln Trp Tyr Met Ile Asp Ile
            95              100             105

Cys Leu Gly Tyr Lys Gly Lys Arg Lys Ile His Thr Val Ile Tyr
            110             115             120

Asp Ser Leu Lys Lys Leu Pro Phe Pro Val Lys Lys Ile Ala Lys
            125             130             135

Asp Phe Lys Leu Thr Val Leu Lys Gly Asp Ile Asp Tyr His Lys
            140             145             150

Glu Arg Pro Val Gly Tyr Lys Ile Thr Pro Glu Glu Tyr Ala Tyr
            155             160             165

Ile Lys Asn Asp Ile Gln Ile Ile Ala Glu Ala Leu Leu Ile Gln
            170             175             180

Phe Lys Gln Gly Leu Asp Arg Met Thr Ala Gly Ser Asp Ser Leu
            185             190             195

Lys Gly Phe Lys Asp Ile Ile Thr Thr Lys Lys Phe Lys Lys Val
            200             205             210

Phe Pro Thr Leu Ser Leu Gly Leu Asp Lys Glu Val Arg Tyr Ala
            215             220             225

Tyr Arg Gly Gly Phe Thr Trp Leu Asn Asp Arg Phe Lys Glu Lys
            230             235             240

Glu Ile Gly Glu Gly Met Val Phe Asp Val Asn Ser Leu Tyr Pro
            245             250             255

Ala Gln Met Tyr Ser Arg Leu Leu Pro Tyr Gly Glu Pro Ile Val
            260             265             270

Phe Glu Gly Lys Tyr Val Trp Asp Glu Asp Tyr Pro Leu His Ile
            275             280             285
```

-continued

```
Gln His Ile Arg Cys Glu Phe Glu Leu Lys Glu Gly Tyr Ile Pro
              290                 295                 300

Thr Ile Gln Ile Lys Arg Ser Arg Phe Tyr Lys Gly Asn Glu Tyr
              305                 310                 315

Leu Lys Ser Ser Gly Gly Glu Ile Ala Asp Leu Trp Leu Ser Asn
              320                 325                 330

Val Asp Leu Glu Leu Met Lys Glu His Tyr Asp Leu Tyr Asn Val
              335                 340                 345

Glu Tyr Ile Ser Gly Leu Lys Phe Lys Ala Thr Thr Gly Leu Phe
              350                 355                 360

Lys Asp Phe Ile Asp Lys Trp Thr Tyr Ile Lys Thr Thr Ser Glu
              365                 370                 375

Gly Ala Ile Lys Gln Leu Ala Lys Leu Met Leu Asn Ser Leu Tyr
              380                 385                 390

Gly Lys Phe Ala Ser Asn Pro Asp Val Thr Gly Lys Val Pro Tyr
              395                 400                 405

Leu Lys Glu Asn Gly Ala Leu Gly Phe Arg Leu Gly Glu Glu Glu
              410                 415                 420

Thr Lys Asp Pro Val Tyr Thr Pro Met Gly Val Phe Ile Thr Ala
              425                 430                 435

Trp Ala Arg Tyr Thr Thr Ile Thr Ala Ala Gln Ala Cys Tyr Asp
              440                 445                 450

Arg Ile Ile Tyr Cys Asp Thr Asp Ser Ile His Leu Thr Gly Thr
              455                 460                 465

Glu Ile Pro Asp Val Ile Lys Asp Ile Val Asp Pro Lys Lys Leu
              470                 475                 480

Gly Tyr Trp Ala His Glu Ser Thr Phe Lys Arg Ala Lys Tyr Leu
              485                 490                 495

Arg Gln Lys Thr Tyr Ile Gln Asp Ile Tyr Met Lys Glu Val Asp
              500                 505                 510

Gly Lys Leu Val Glu Gly Ser Pro Asp Asp Tyr Thr Asp Ile Lys
              515                 520                 525

Phe Ser Val Lys Cys Ala Gly Met Thr Asp Lys Ile Lys Lys Glu
              530                 535                 540

Val Thr Phe Glu Asn Phe Lys Val Gly Phe Ser Arg Lys Met Lys
              545                 550                 555

Pro Lys Pro Val Gln Val Pro Gly Gly Val Val Leu Val Asp Asp
              560                 565                 570

Thr Phe Thr Ile Lys
              575
```

SEQ ID NO 4: K64R/M97K Phi29DNApol double mutant

```
Met Lys His Met Pro Arg Lys Met Tyr Ser Cys Asp Phe Glu Thr
1                 5                 10                  15

Thr Thr Lys Val Glu Asp Cys Arg Val Trp Ala Tyr Gly Tyr Met
              20                  25                  30

Asn Ile Glu Asp His Ser Glu Tyr Lys Ile Gly Asn Ser Leu Asp
              35                  40                  45

Glu Phe Met Ala Trp Val Leu Lys Val Gln Ala Asp Leu Tyr Phe
              50                  55                  60

His Asn Leu Arg Phe Asp Gly Ala Phe Ile Ile Asn Trp Leu Glu
              65                  70                  75

Arg Asn Gly Phe Lys Trp Ser Ala Asp Gly Leu Pro Asn Thr Tyr
              80                  85                  90
```

-continued

```
Asn Thr Ile Ile Ser Arg Lys Gly Gln Trp Tyr Met Ile Asp Ile
            95                 100                 105

Cys Leu Gly Tyr Lys Gly Lys Arg Lys Ile His Thr Val Ile Tyr
            110                 115                 120

Asp Ser Leu Lys Lys Leu Pro Phe Pro Val Lys Lys Ile Ala Lys
            125                 130                 135

Asp Phe Lys Leu Thr Val Leu Lys Gly Asp Ile Asp Tyr His Lys
            140                 145                 150

Glu Arg Pro Val Gly Tyr Lys Ile Thr Pro Glu Glu Tyr Ala Tyr
            155                 160                 165

Ile Lys Asn Asp Ile Gln Ile Ile Ala Glu Ala Leu Leu Ile Gln
            170                 175                 180

Phe Lys Gln Gly Leu Asp Arg Met Thr Ala Gly Ser Asp Ser Leu
            185                 190                 195

Lys Gly Phe Lys Asp Ile Ile Thr Thr Lys Lys Phe Lys Lys Val
            200                 205                 210

Phe Pro Thr Leu Ser Leu Gly Leu Asp Lys Glu Val Arg Tyr Ala
            215                 220                 225

Tyr Arg Gly Gly Phe Thr Trp Leu Asn Asp Arg Phe Lys Glu Lys
            230                 235                 240

Glu Ile Gly Glu Gly Met Val Phe Asp Val Asn Ser Leu Tyr Pro
            245                 250                 255

Ala Gln Met Tyr Ser Arg Leu Leu Pro Tyr Gly Glu Pro Ile Val
            260                 265                 270

Phe Glu Gly Lys Tyr Val Trp Asp Glu Asp Tyr Pro Leu His Ile
            275                 280                 285

Gln His Ile Arg Cys Glu Phe Glu Leu Lys Glu Gly Tyr Ile Pro
            290                 295                 300

Thr Ile Gln Ile Lys Arg Ser Arg Phe Tyr Lys Gly Asn Glu Tyr
            305                 310                 315

Leu Lys Ser Ser Gly Gly Glu Ile Ala Asp Leu Trp Leu Ser Asn
            320                 325                 330

Val Asp Leu Glu Leu Met Lys Glu His Tyr Asp Leu Tyr Asn Val
            335                 340                 345

Glu Tyr Ile Ser Gly Leu Lys Phe Lys Ala Thr Thr Gly Leu Phe
            350                 355                 360

Lys Asp Phe Ile Asp Lys Trp Thr Tyr Ile Lys Thr Thr Ser Glu
            365                 370                 375

Gly Ala Ile Lys Gln Leu Ala Lys Leu Met Leu Asn Ser Leu Tyr
            380                 385                 390

Gly Lys Phe Ala Ser Asn Pro Asp Val Thr Gly Lys Val Pro Tyr
            395                 400                 405

Leu Lys Glu Asn Gly Ala Leu Gly Phe Arg Leu Gly Glu Glu Glu
            410                 415                 420

Thr Lys Asp Pro Val Tyr Thr Pro Met Gly Val Phe Ile Thr Ala
            425                 430                 435

Trp Ala Arg Tyr Thr Thr Ile Thr Ala Ala Gln Ala Cys Tyr Asp
            440                 445                 450

Arg Ile Ile Tyr Cys Asp Thr Asp Ser Ile His Leu Thr Gly Thr
            455                 460                 465

Glu Ile Pro Asp Val Ile Lys Asp Ile Val Asp Pro Lys Lys Leu
            470                 475                 480

Gly Tyr Trp Ala His Glu Ser Thr Phe Lys Arg Ala Lys Tyr Leu
            485                 490                 495
```

-continued

```
Arg Gln Lys Thr Tyr Ile Gln Asp Ile Tyr Met Lys Glu Val Asp
                500                 505                 510

Gly Lys Leu Val Glu Gly Ser Pro Asp Asp Tyr Thr Asp Ile Lys
                515                 520                 525

Phe Ser Val Lys Cys Ala Gly Met Thr Asp Lys Ile Lys Lys Glu
                530                 535                 540

Val Thr Phe Glu Asn Phe Lys Val Gly Phe Ser Arg Lys Met Lys
                545                 550                 555

Pro Lys Pro Val Gln Val Pro Gly Gly Val Val Leu Val Asp Asp
                560                 565                 570

Thr Phe Thr Ile Lys
                575
```

What is claimed is:

1. A Phi29 type DNA polymerase that comprises amino acid substitution K64R, and M97K.

2. The Phi29 type DNA polymerase of claim 1 having an amino acid sequence of SEQ ID NO; 4.

3. A method for replicating, amplifying or sequencing a template DNA which comprises contacting said DNA with a reaction mixture comprising at least:

a) the DNA polymerase according to claim 1, b) a buffer, c) magnesium chloride, d) a primer, and e) nucleoside triphosphates.

4. A Phi29 type DNA polymerase, wherein the Phi29 type DNA polymerase has an amino acid sequence having at least 80%, 85%, 90%, 95%, 98%, 99%, or 99.5% sequence identity with SEQ ID NO:1, and wherein the Phi29 type DNA polymerase comprises amino acid substitution K64R, and M97K.

5. The Phi29 type DNA polymerase of claim 4, having no more than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions, additions or deletions in addition to amino acid substitution K64R, and M97K.

6. A method comprising:

a) contacting a nucleic acid template molecule with a Phi29 type DNA polymerase of claim 1, and reagents sufficient for primer extension; and b) performing primer extension with the polymerase using the nucleic acid template.

7. The method of claim 6, wherein the reagents sufficient for primer extension comprise oligonucleotide primers.

8. The method of claim 7, wherein the oligonucleotide primers comprise one or more of trimers, tetramers, pentamers, hexamers, heptamers, octamers, nanomers or 10-mers.

9. The method of claim 8, wherein the primers are random primers.

10. The method of claim 7, wherein the oligonucleotide primers have lengths between five and 25 nucleotides.

11. The method of claim 6, wherein the reagents sufficient for primer extension comprise a primase/polymerase.

12. The method of claim 6, wherein primer extension is performed at a temperature about, or above, any of 31° C., 32° C., 33° C., 34° C., 35° C., 36° C., 37° C., 38° C., 39° C., 40° C., 41° C., or 42° C.

13. The method of claim 6, wherein the template nucleic acid molecule is present in an amount no greater than 1 ng, 100 µg, 10 pg, or 1 pg.

14. The method of claim 6, wherein the primer extension comprises (i) multiple displacement amplification ("MDA") or (ii) rolling circle amplification.

15. The method of claim 6, wherein the primer extension comprises multiple annealing and looping-based amplification cycles (MALBAC).

* * * * *

SEQUENCE LISTING

<160> NUMBER OF SEQ ID NOS: 6

<210> SEQ ID NO 1
<211> LENGTH: 575
<212> TYPE: PRT
<213> ORGANISM: Bacillus subtilis
<220> FEATURE:
<223> OTHER INFORMATION: Phi29DNApol wild type

<400> SEQUENCE: 1

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
        210                 215                 220

Ala Tyr Arg Gly Gly Phe Thr Trp Leu Asn Asp Arg Phe Lys Glu Lys
225                 230                 235                 240
```

-continued

```
Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
        530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575
```

```
<210> SEQ ID NO 2
<211> LENGTH: 575
<212> TYPE: PRT
<213> ORGANISM: Artificial Sequence
<220> FEATURE:
<223> OTHER INFORMATION: K64R Phi29DNApol mutant

<400> SEQUENCE: 2

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30
```

```
Glu Asp His Ser Glu Tyr Lys Ile Gly Asn Ser Leu Asp Glu Phe Met
        35              40              45

Ala Trp Val Leu Lys Val Gln Ala Asp Leu Tyr Phe His Asn Leu Arg
    50              55              60

Phe Asp Gly Ala Phe Ile Ile Asn Trp Leu Glu Arg Asn Gly Phe Lys
65              70              75              80

Trp Ser Ala Asp Gly Leu Pro Asn Thr Tyr Asn Thr Ile Ile Ser Arg
                85              90              95

Met Gly Gln Trp Tyr Met Ile Asp Ile Cys Leu Gly Tyr Lys Gly Lys
            100             105             110

Arg Lys Ile His Thr Val Ile Tyr Asp Ser Leu Lys Lys Leu Pro Phe
            115             120             125

Pro Val Lys Lys Ile Ala Lys Asp Phe Lys Leu Thr Val Leu Lys Gly
    130             135             140

Asp Ile Asp Tyr His Lys Glu Arg Pro Val Gly Tyr Lys Ile Thr Pro
145             150             155             160

Glu Glu Tyr Ala Tyr Ile Lys Asn Asp Ile Gln Ile Ile Ala Glu Ala
            165             170             175

Leu Leu Ile Gln Phe Lys Gln Gly Leu Asp Arg Met Thr Ala Gly Ser
            180             185             190

Asp Ser Leu Lys Gly Phe Lys Asp Ile Ile Thr Thr Lys Lys Phe Lys
            195             200             205

Lys Val Phe Pro Thr Leu Ser Leu Gly Leu Asp Lys Glu Val Arg Tyr
    210             215             220

Ala Tyr Arg Gly Gly Phe Thr Trp Leu Asn Asp Arg Phe Lys Glu Lys
225             230             235             240

Glu Ile Gly Glu Gly Met Val Phe Asp Val Asn Ser Leu Tyr Pro Ala
            245             250             255

Gln Met Tyr Ser Arg Leu Leu Pro Tyr Gly Glu Pro Ile Val Phe Glu
            260             265             270

Gly Lys Tyr Val Trp Asp Glu Asp Tyr Pro Leu His Ile Gln His Ile
            275             280             285

Arg Cys Glu Phe Glu Leu Lys Glu Gly Tyr Ile Pro Thr Ile Gln Ile
    290             295             300

Lys Arg Ser Arg Phe Tyr Lys Gly Asn Glu Tyr Leu Lys Ser Ser Gly
305             310             315             320

Gly Glu Ile Ala Asp Leu Trp Leu Ser Asn Val Asp Leu Glu Leu Met
            325             330             335

Lys Glu His Tyr Asp Leu Tyr Asn Val Glu Tyr Ile Ser Gly Leu Lys
            340             345             350

Phe Lys Ala Thr Thr Gly Leu Phe Lys Asp Phe Ile Asp Lys Trp Thr
            355             360             365

Tyr Ile Lys Thr Thr Ser Glu Gly Ala Ile Lys Gln Leu Ala Lys Leu
    370             375             380

Met Leu Asn Ser Leu Tyr Gly Lys Phe Ala Ser Asn Pro Asp Val Thr
385             390             395             400

Gly Lys Val Pro Tyr Leu Lys Glu Asn Gly Ala Leu Gly Phe Arg Leu
            405             410             415

Gly Glu Glu Glu Thr Lys Asp Pro Val Tyr Thr Pro Met Gly Val Phe
            420             425             430

Ile Thr Ala Trp Ala Arg Tyr Thr Thr Ile Thr Ala Ala Gln Ala Cys
            435             440             445

Tyr Asp Arg Ile Ile Tyr Cys Asp Thr Asp Ser Ile His Leu Thr Gly
```

-continued

```
         450              455              460
Thr Glu Ile Pro Asp Val Ile Lys Asp Ile Val Asp Pro Lys Lys Leu
465                   470              475              480

Gly Tyr Trp Ala His Glu Ser Thr Phe Lys Arg Ala Lys Tyr Leu Arg
                485              490              495

Gln Lys Thr Tyr Ile Gln Asp Ile Tyr Met Lys Glu Val Asp Gly Lys
                500              505              510

Leu Val Glu Gly Ser Pro Asp Asp Tyr Thr Asp Ile Lys Phe Ser Val
            515              520              525

Lys Cys Ala Gly Met Thr Asp Lys Ile Lys Lys Glu Val Thr Phe Glu
        530              535              540

Asn Phe Lys Val Gly Phe Ser Arg Lys Met Lys Pro Lys Pro Val Gln
545              550              555              560

Val Pro Gly Gly Val Val Leu Val Asp Asp Thr Phe Thr Ile Lys
            565              570              575

<210> SEQ ID NO 3
<211> LENGTH: 575
<212> TYPE: PRT
<213> ORGANISM: Artificial Sequence
<220> FEATURE:
<223> OTHER INFORMATION: M97K Phi29DNApol mutant

<400> SEQUENCE: 3

Met Lys His Met Pro Arg Lys Met Tyr Ser Cys Asp Phe Glu Thr Thr
1                5              10              15

Thr Lys Val Glu Asp Cys Arg Val Trp Ala Tyr Gly Tyr Met Asn Ile
            20              25              30

Glu Asp His Ser Glu Tyr Lys Ile Gly Asn Ser Leu Asp Glu Phe Met
        35              40              45

Ala Trp Val Leu Lys Val Gln Ala Asp Leu Tyr Phe His Asn Leu Lys
    50              55              60

Phe Asp Gly Ala Phe Ile Ile Asn Trp Leu Glu Arg Asn Gly Phe Lys
65              70              75              80

Trp Ser Ala Asp Gly Leu Pro Asn Thr Tyr Asn Thr Ile Ile Ser Arg
            85              90              95

Lys Gly Gln Trp Tyr Met Ile Asp Ile Cys Leu Gly Tyr Lys Gly Lys
            100              105              110

Arg Lys Ile His Thr Val Ile Tyr Asp Ser Leu Lys Lys Leu Pro Phe
            115              120              125

Pro Val Lys Lys Ile Ala Lys Asp Phe Lys Leu Thr Val Leu Lys Gly
        130              135              140

Asp Ile Asp Tyr His Lys Glu Arg Pro Val Gly Tyr Lys Ile Thr Pro
145              150              155              160

Glu Glu Tyr Ala Tyr Ile Lys Asn Asp Ile Gln Ile Ile Ala Glu Ala
                165              170              175

Leu Leu Ile Gln Phe Lys Gln Gly Leu Asp Arg Met Thr Ala Gly Ser
            180              185              190

Asp Ser Leu Lys Gly Phe Lys Asp Ile Ile Thr Thr Lys Lys Phe Lys
            195              200              205

Lys Val Phe Pro Thr Leu Ser Leu Gly Leu Asp Lys Glu Val Arg Tyr
        210              215              220

Ala Tyr Arg Gly Gly Phe Thr Trp Leu Asn Asp Arg Phe Lys Glu Lys
225              230              235              240

Glu Ile Gly Glu Gly Met Val Phe Asp Val Asn Ser Leu Tyr Pro Ala
```

-continued

```
              245              250              255

Gln Met Tyr Ser Arg Leu Leu Pro Tyr Gly Glu Pro Ile Val Phe Glu
          260              265              270

Gly Lys Tyr Val Trp Asp Glu Asp Tyr Pro Leu His Ile Gln His Ile
          275              280              285

Arg Cys Glu Phe Glu Leu Lys Glu Gly Tyr Ile Pro Thr Ile Gln Ile
      290              295              300

Lys Arg Ser Arg Phe Tyr Lys Gly Asn Glu Tyr Leu Lys Ser Ser Gly
  305              310              315              320

Gly Glu Ile Ala Asp Leu Trp Leu Ser Asn Val Asp Leu Glu Leu Met
              325              330              335

Lys Glu His Tyr Asp Leu Tyr Asn Val Glu Tyr Ile Ser Gly Leu Lys
          340              345              350

Phe Lys Ala Thr Thr Gly Leu Phe Lys Asp Phe Ile Asp Lys Trp Thr
          355              360              365

Tyr Ile Lys Thr Thr Ser Glu Gly Ala Ile Lys Gln Leu Ala Lys Leu
      370              375              380

Met Leu Asn Ser Leu Tyr Gly Lys Phe Ala Ser Asn Pro Asp Val Thr
  385              390              395              400

Gly Lys Val Pro Tyr Leu Lys Glu Asn Gly Ala Leu Gly Phe Arg Leu
              405              410              415

Gly Glu Glu Glu Thr Lys Asp Pro Val Tyr Thr Pro Met Gly Val Phe
          420              425              430

Ile Thr Ala Trp Ala Arg Tyr Thr Thr Ile Thr Ala Ala Gln Ala Cys
          435              440              445

Tyr Asp Arg Ile Ile Tyr Cys Asp Thr Asp Ser Ile His Leu Thr Gly
      450              455              460

Thr Glu Ile Pro Asp Val Ile Lys Asp Ile Val Asp Pro Lys Lys Leu
  465              470              475              480

Gly Tyr Trp Ala His Glu Ser Thr Phe Lys Arg Ala Lys Tyr Leu Arg
              485              490              495

Gln Lys Thr Tyr Ile Gln Asp Ile Tyr Met Lys Glu Val Asp Gly Lys
          500              505              510

Leu Val Glu Gly Ser Pro Asp Asp Tyr Thr Asp Ile Lys Phe Ser Val
          515              520              525

Lys Cys Ala Gly Met Thr Asp Lys Ile Lys Lys Glu Val Thr Phe Glu
      530              535              540

Asn Phe Lys Val Gly Phe Ser Arg Lys Met Lys Pro Lys Pro Val Gln
  545              550              555              560

Val Pro Gly Gly Val Val Leu Val Asp Asp Thr Phe Thr Ile Lys
              565              570              575

<210> SEQ ID NO 4
<211> LENGTH: 575
<212> TYPE: PRT
<213> ORGANISM: Artificial Sequence
<220> FEATURE:
<223> OTHER INFORMATION: K64R / M97K Phi29DNApol double mutant

<400> SEQUENCE: 4

Met Lys His Met Pro Arg Lys Met Tyr Ser Cys Asp Phe Glu Thr Thr
1               5               10              15

Thr Lys Val Glu Asp Cys Arg Val Trp Ala Tyr Gly Tyr Met Asn Ile
          20              25              30

Glu Asp His Ser Glu Tyr Lys Ile Gly Asn Ser Leu Asp Glu Phe Met
```

```
              35                    40                    45
Ala Trp Val Leu Lys Val Gln Ala Asp Leu Tyr Phe His Asn Leu Arg
    50                    55                    60

Phe Asp Gly Ala Phe Ile Ile Asn Trp Leu Glu Arg Asn Gly Phe Lys
65                    70                    75                    80

Trp Ser Ala Asp Gly Leu Pro Asn Thr Tyr Asn Thr Ile Ile Ser Arg
                  85                    90                    95

Lys Gly Gln Trp Tyr Met Ile Asp Ile Cys Leu Gly Tyr Lys Gly Lys
                  100                   105                   110

Arg Lys Ile His Thr Val Ile Tyr Asp Ser Leu Lys Lys Leu Pro Phe
              115                   120                   125

Pro Val Lys Lys Ile Ala Lys Asp Phe Lys Leu Thr Val Leu Lys Gly
    130                   135                   140

Asp Ile Asp Tyr His Lys Glu Arg Pro Val Gly Tyr Lys Ile Thr Pro
145                   150                   155                   160

Glu Glu Tyr Ala Tyr Ile Lys Asn Asp Ile Gln Ile Ile Ala Glu Ala
                  165                   170                   175

Leu Leu Ile Gln Phe Lys Gln Gly Leu Asp Arg Met Thr Ala Gly Ser
              180                   185                   190

Asp Ser Leu Lys Gly Phe Lys Asp Ile Ile Thr Thr Lys Lys Phe Lys
              195                   200                   205

Lys Val Phe Pro Thr Leu Ser Leu Gly Leu Asp Lys Glu Val Arg Tyr
    210                   215                   220

Ala Tyr Arg Gly Gly Phe Thr Trp Leu Asn Asp Arg Phe Lys Glu Lys
225                   230                   235                   240

Glu Ile Gly Glu Gly Met Val Phe Asp Val Asn Ser Leu Tyr Pro Ala
                  245                   250                   255

Gln Met Tyr Ser Arg Leu Leu Pro Tyr Gly Glu Pro Ile Val Phe Glu
                  260                   265                   270

Gly Lys Tyr Val Trp Asp Glu Asp Tyr Pro Leu His Ile Gln His Ile
              275                   280                   285

Arg Cys Glu Phe Glu Leu Lys Glu Gly Tyr Ile Pro Thr Ile Gln Ile
    290                   295                   300

Lys Arg Ser Arg Phe Tyr Lys Gly Asn Glu Tyr Leu Lys Ser Ser Gly
305                   310                   315                   320

Gly Glu Ile Ala Asp Leu Trp Leu Ser Asn Val Asp Leu Glu Leu Met
                  325                   330                   335

Lys Glu His Tyr Asp Leu Tyr Asn Val Glu Tyr Ile Ser Gly Leu Lys
              340                   345                   350

Phe Lys Ala Thr Thr Gly Leu Phe Lys Asp Phe Ile Asp Lys Trp Thr
              355                   360                   365

Tyr Ile Lys Thr Thr Ser Glu Gly Ala Ile Lys Gln Leu Ala Lys Leu
    370                   375                   380

Met Leu Asn Ser Leu Tyr Gly Lys Phe Ala Ser Asn Pro Asp Val Thr
385                   390                   395                   400

Gly Lys Val Pro Tyr Leu Lys Glu Asn Gly Ala Leu Gly Phe Arg Leu
                  405                   410                   415

Gly Glu Glu Glu Thr Lys Asp Pro Val Tyr Thr Pro Met Gly Val Phe
              420                   425                   430

Ile Thr Ala Trp Ala Arg Tyr Thr Thr Ile Thr Ala Ala Gln Ala Cys
              435                   440                   445

Tyr Asp Arg Ile Ile Tyr Cys Asp Thr Asp Ser Ile His Leu Thr Gly
    450                   455                   460
```

-continued

```
Thr Glu Ile Pro Asp Val Ile Lys Asp Ile Val Asp Pro Lys Lys Leu
465             470             475             480

Gly Tyr Trp Ala His Glu Ser Thr Phe Lys Arg Ala Lys Tyr Leu Arg
            485             490             495

Gln Lys Thr Tyr Ile Gln Asp Ile Tyr Met Lys Glu Val Asp Gly Lys
            500             505             510

Leu Val Glu Gly Ser Pro Asp Asp Tyr Thr Asp Ile Lys Phe Ser Val
            515             520             525

Lys Cys Ala Gly Met Thr Asp Lys Ile Lys Lys Glu Val Thr Phe Glu
            530             535             540

Asn Phe Lys Val Gly Phe Ser Arg Lys Met Lys Pro Lys Pro Val Gln
545             550             555             560

Val Pro Gly Gly Val Val Leu Val Asp Asp Thr Phe Thr Ile Lys
            565             570             575

<210> SEQ ID NO 5
<211> LENGTH: 15
<212> TYPE: DNA
<213> ORGANISM: Artificial Sequence
<220> FEATURE:
<223> OTHER INFORMATION: 5'-labelled primer of DNA duplex

<400> SEQUENCE: 5
gatcacagtg agtac                                                    15

<210> SEQ ID NO 6
<211> LENGTH: 28
<212> TYPE: DNA
<213> ORGANISM: Artificial Sequence
<220> FEATURE:
<223> OTHER INFORMATION: template of DNA duplex

<400> SEQUENCE: 6
agaagtgtat ctggtactca ctgtgatc                                      28
```